(12) United States Patent
Mitchell

(10) Patent No.: US 11,974,748 B2
(45) Date of Patent: May 7, 2024

(54) SYSTEM AND METHOD FOR ATTACHING A FLUID CONDUIT TO AN ANATOMICAL STRUCTURE

(71) Applicant: The Regents of the University of Colorado, Denver, CO (US)

(72) Inventor: Max Bannister Mitchell, Castle Pines, CO (US)

(73) Assignee: The Regents of the University of Colorado, Denver, CO (US)

(*) Notice: Subject to any disclaimer, the term of this patent is extended or adjusted under 35 U.S.C. 154(b) by 1036 days.

(21) Appl. No.: 16/739,807

(22) Filed: Jan. 10, 2020

(65) Prior Publication Data

US 2020/0253606 A1 Aug. 13, 2020

Related U.S. Application Data

(60) Provisional application No. 62/791,264, filed on Jan. 11, 2019.

(51) Int. Cl.
*A61B 17/11* (2006.01)
*A61B 17/064* (2006.01)
(Continued)

(52) U.S. Cl.
CPC ............ *A61B 17/11* (2013.01); *A61B 17/064* (2013.01); *A61F 2/07* (2013.01); *A61M 60/178* (2021.01); *A61M 60/216* (2021.01); *A61M 60/857* (2021.01); *A61M 60/859* (2021.01); *A61M 60/861* (2021.01); *A61B 2017/00867* (2013.01);
(Continued)

(58) Field of Classification Search
CPC ..... A61B 17/11; A61B 17/064; A61B 17/115; A61B 2017/00867; A61B 2017/1107; A61B 2017/1135; A61F 2/07; A61F 2230/0095; A61M 60/178; A61M 60/216;
(Continued)

(56) References Cited

U.S. PATENT DOCUMENTS

| 5,700,285 A | 12/1997 | Myers et al. ...................... 623/1 |
| 6,190,590 B1 | 2/2001 | Randall et al. ................ 264/138 |

(Continued)

FOREIGN PATENT DOCUMENTS

| EP | 1266628 | 12/2002 | ........... A61B 17/064 |
| WO | 1997-028749 | 8/1997 | ........... A61B 17/068 |

(Continued)

OTHER PUBLICATIONS

International Search Report and Written Opinion issued in corresponding foreign application, PCT/US2020/013135, pp. 1-18 (dated Jul. 10, 2020).

*Primary Examiner* — Jing Rui Ou
(74) *Attorney, Agent, or Firm* — Rosenbaum IP, P.C.; David G. Rosenbaum

(57) ABSTRACT

A system and method for end-to-side anastomosis to an anatomical passageway is disclosed. The system and method are particularly useful in coupling an LVAD pump to an aorta. The system and method include using a tubular graft member having a skirt flange that engages the side of the aorta, a seating assembly and a flanged stent for securing the tubular graft to the side of the anatomical passageway. An assembly for creating an opening in the side of the anatomical passageway and an assembly for delivering the tubular graft is also disclosed.

10 Claims, 34 Drawing Sheets

(51) Int. Cl.
  *A61F 2/07* (2013.01)
  *A61M 60/178* (2021.01)
  *A61M 60/216* (2021.01)
  *A61M 60/857* (2021.01)
  *A61M 60/859* (2021.01)
  *A61M 60/861* (2021.01)
  *A61B 17/00* (2006.01)
  *A61B 17/115* (2006.01)

(52) U.S. Cl.
  CPC ............ *A61B 2017/1107* (2013.01); *A61B 2017/1135* (2013.01); *A61B 17/115* (2013.01); *A61F 2230/0095* (2013.01)

(58) Field of Classification Search
  CPC . A61M 60/857; A61M 60/859; A61M 60/861
  See application file for complete search history.

(56) References Cited

U.S. PATENT DOCUMENTS

| | | | |
|---|---|---|---|
| 6,203,735 B1 | 3/2001 | Edwin et al. | 264/127 |
| 6,273,912 B1 | 8/2001 | Scholz et al. | 623/1.31 |
| 6,383,214 B1 | 5/2002 | Banas et al. | 623/1.14 |
| 6,652,578 B2 | 11/2003 | Bailey et al. | 623/1.24 |
| 7,794,471 B1 | 9/2010 | Bender et al. | 606/153 |
| 9,445,886 B2 | 9/2016 | Harris et al. | A61F 2/064 |
| 10,335,527 B2 | 7/2019 | Mitchell et al. | A61M 1/1008 |
| 2001/0041902 A1* | 11/2001 | Lepulu | A61F 2/94 |
| | | | 606/153 |
| 2005/0192604 A1 | 9/2005 | Carson et al. | 606/153 |
| 2008/0195125 A1* | 8/2008 | Hoffman | A61B 17/11 |
| | | | 606/153 |
| 2009/0076531 A1* | 3/2009 | Richardson | A61B 17/11 |
| | | | 623/1.1 |
| 2010/0130995 A1* | 5/2010 | Yevzlin | A61B 17/11 |
| | | | 606/153 |
| 2010/0161040 A1 | 6/2010 | Braido et al. | 623/2.1 |
| 2011/0118764 A1* | 5/2011 | Beane | A61B 17/11 |
| | | | 606/153 |
| 2012/0296151 A1 | 11/2012 | Curtis et al. | 600/16 |
| 2014/0343582 A1 | 11/2014 | Asfora et al. | A61B 17/11 |
| 2015/0012006 A1 | 1/2015 | Hausen et al. | A61B 17/115 |

FOREIGN PATENT DOCUMENTS

| | | | | |
|---|---|---|---|---|
| WO | 2001-000108 | | 1/2001 | ............ A61F 2/06 |
| WO | 2002-034143 | | 5/2002 | ............ A61B 17/11 |

\* cited by examiner

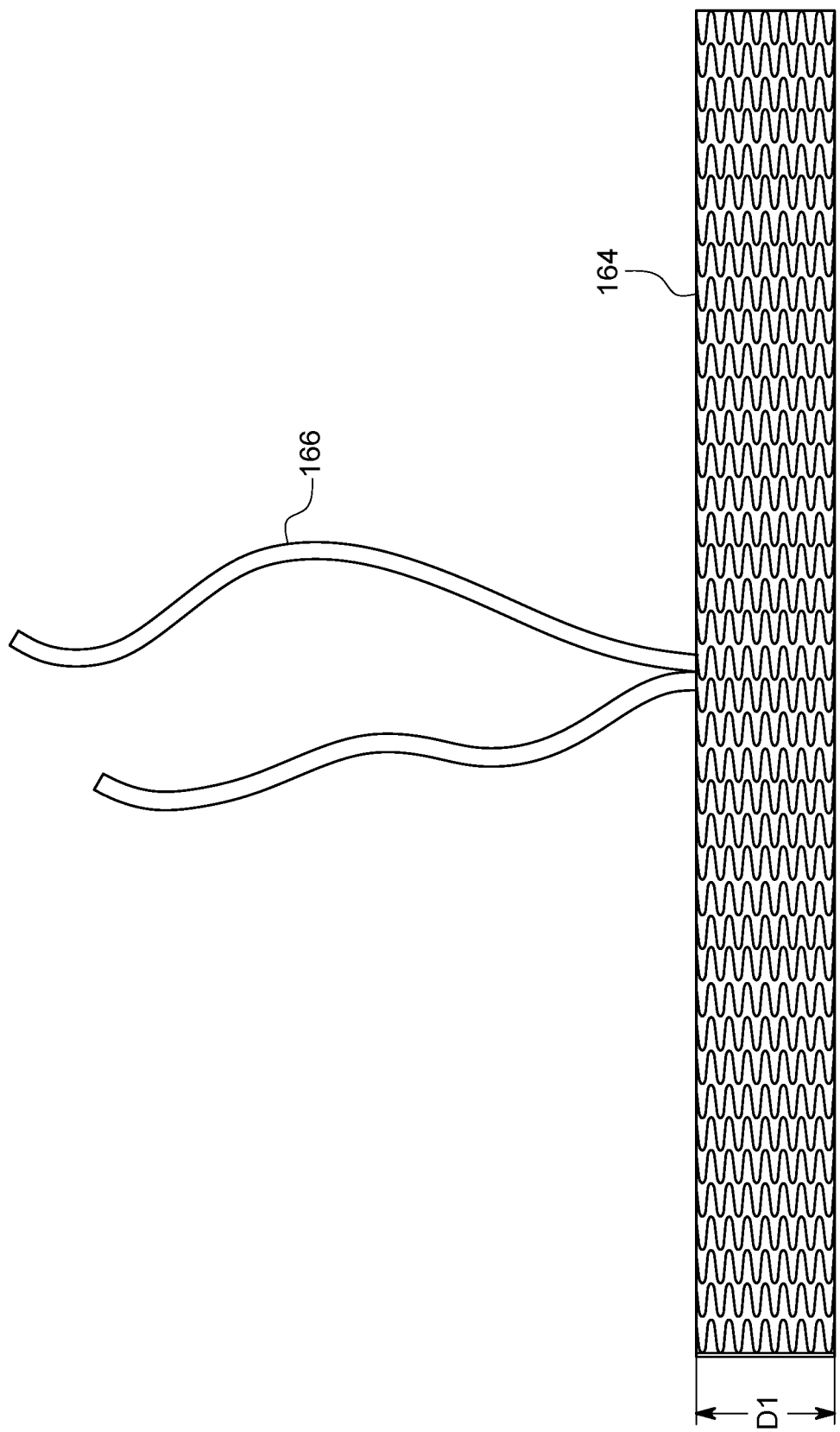

SYSTEM AND METHOD FOR ATTACHING A FLUID CONDUIT TO AN ANATOMICAL STRUCTURE

CROSS-REFERENCE TO RELATED APPLICATIONS

This application is related to and claims priority to U.S. Provisional Patent Application Ser. No. 62/791,264 filed Jan. 11, 2019.

STATEMENT OF GOVERNMENT INTEREST

None

BACKGROUND OF THE INVENTION

The present invention pertains generally to devices and methods for making end-to-side connections between a tubular fluid conduit and another tubular structure. More particularly, the present invention pertains to medical devices and methods for making an end-to-side anastomosis between a tubular structure and an anatomic structure. Even more particularly, the present invention relates to a tubular medical graft having a flared or flanged end, a system for creating an end-to-side anastomosis with an anatomical structure, such as a blood vessel, and a method for creating the end-to-side anastomosis. One exemplary medical application of the present invention is to create an end-to-side anastomosis to attach a flared or flanged end tubular medical graft to an aorta of a patient in need thereof, couple the flared or flanged end to the aorta, and couple an opposing end of the tubular medical graft to a fluid conduit from a ventricular assist device ("VAD") such as a left ventricular assist device ("LVAD") to create a fluid path from the VAD to the aorta. It will be understood that other non-medical applications of the devices and methods are also intended and contemplated by the present disclosure and that the medical application to VAD devices is intended to be a non-limiting example of an application of the devices and methods described herein.

Heart failure is a leading cause of death in developed countries. An estimated 100,000 Americans develop end-stage congestive heart failure each year with a one-year mortality of approximately 50%. There are many etiologies of heart failure. Treatment options depend on the underlying cause and consist of drug therapy, catheter based or surgical interventions for coronary artery disease, and catheter or surgical procedures for valve disease and other lesions. In the past, the only treatment for end-stage non-correctable heart failure was heart transplantation. Approximately 2,000 heart transplant procedures are performed annually in the United States and approximately 5,000 are performed annually world-wide. At any given time, there are approximately 3,000 patients on the heart transplant waiting list in the United States. Consequently, demand for transplantation far outstrips the supply of donor hearts, and it is unlikely that this supply imbalance will improve. Because of the donor supply imbalance, practitioners have developed mechanical VAD systems to support the circulation in patients with heart failure.

Initially, VAD therapy was limited to heart transplant candidates and was intended to bridge patients to heart transplant and improve their baseline health status going into transplant. This strategy is commonly referred to as Bridge to Transplant ("BTT"). As technology improved, VAD outcomes improved and VAD therapy was extended to the larger population of heart failure patients who are not candidates for transplant. VAD treatment in the latter pool of patients is referred to as Destination Treatment ("DT"). Most patients, regardless of treatment intent, can be supported with a left sided device alone.

The current generation of LVADs in common use are continuous flow devices. The newer continuous flow LVADs are small enough to be implanted entirely within the pericardial space and do not require an intra-abdominal pocket. In general, the pumping inlet mechanism of current LVADs is surgically attached directly to a heart chamber. The outflow end of the pumping mechanism consists of a prosthetic vascular tube graft that is sewn end to side to a major artery—usually the ascending aorta. There are other surgical indications for the attachment of the end of a large prosthetic vascular graft to the side of a major artery. For example, ascending aorta to descending aorta bypass procedures require end to side attachment of a prosthetic graft to the ascending aorta at one end and the descending aorta at the other end. An alternative example of an application for the end-to-side anastomosis system is in implanting an apical-aortic valve conduit in which a valved conduit is implanted into the left ventricular apex and then a distal end of the valved conduit is joined by an end-to-side anastomosis to the descending aorta bypassing the aortic valve.

Most current LVADs are continuous flow devices. These devices typically employ a separate component, called an apical cuff that is first attached to the left ventricular apex and supports attachment of the LVAD pumping device to the left ventricular apex. An apical opening is formed in the ventricular apex central to the apical cuff and the LVAD pumping device is then attached to the apical cuff with a portion of the pumping device passing through the apical opening to communicate with the ventricular chamber. Apical cuffs typically consist of a rigid metal cylinder surrounded by a fabric sewing ring. A device and method for implanting an apical cuff is described in commonly assigned U.S. Pat. No. 10,335,527 issued Jul. 2, 2019, which is hereby incorporated by reference in its entirety as teaching a device and method for apical cuff implantation for the attachment of a ventricular assist device.

Conventional methods for the surgical attachment, e.g., anastomosis, of the end of a large prosthetic tube graft to the side of a major artery typically involve isolating a segment of the target artery with a side-biting clamp or between two completely occlusive clamps. An opening is created in the target artery, known as an arteriotomy, and the prosthetic tube graft is manually sutured to the arteriotomy in an end to side manner with the arteriotomy opening and a central lumen of the prosthetic tube graft being in fluid flow communication with each other. Suturing methods vary and include running suture techniques, interrupted suture techniques, i.e., using a plurality of individually placed and tied sutures, or a combination of these methods. Conventional suturing methods are time consuming, require clamping of the target vessel which in some cases may be diseased, and can be associated with significant bleeding.

While the present invention will be described with respect to its use with a VAD procedure and system, those skilled in the art will understand and appreciate that the scope of the present invention is intended not to be limited to VAD procedures and systems but to end-to-side connections between tubular medical grafts, autologous anatomical tubular grafts, heterologous or other biological tubular grafts, and other anatomical structures, such as the gastrointestinal system, biliary system, lymphatic system, urinary system or the like.

SUMMARY OF THE INVENTION

The currently disclosed devices, system and method for making an end-to-side connection between two tubular conduits, such as attaching a graft to a blood vessel is useful in VAD procedures to fluidly couple a ventricular assist pump joined to the ventricular apex with the aorta.

There is provided a graft configured to be coupled to a circumferential aspect of a blood vessel, such as the aorta. A distal end of the graft has a skirt flange that extends radially outward from a central axis of the graft. The skirt flange may be a pliant material capable of conforming to generally a saddle shape that conforms to the curvature of the blood vessel or anatomical material. Alternatively the skirt flange may be configured to have a generally saddle shape. A proximal end of the graft is configured for end-to-end connection.

There is also provided an anchoring cuff that is circumferentially disposed over a distal end of the graft abutting a proximal surface of the skirt flange and serves as a staple ring for fixing the graft skirt flange to the outer wall of the blood vessel or other anatomical structure. The anchoring cuff may optionally have a radially extending flange that may, optionally, have a saddle-shape that conforms to the circumferential curvature of the target blood vessel or anatomical structure. The anchoring cuff is made of a rigid or semi-rigid material and has a plurality of staple guide openings passing through the anchoring cuff. In accordance with one variant of the anchoring cuff, each staple guide opening is radially offset from the circumferentially adjacent staple guide openings.

A system for delivering and anchoring the graft to the internal wall of the blood vessel or other anatomical structure, is also provided. The delivery and anchoring system includes a stent, a pusher that carries the stent, an inner delivery sheath that covers the pusher and the stent, and an outer delivery sheath having a centering balloon, the pusher and the inner delivery sheath move reciprocally relative to each other to deploy the stent within the graft and the blood vessel or other anatomical structure.

BRIEF DESCRIPTION OF THE DRAWINGS

FIG. 6A is a side elevational view of an end-to-end connector in a diametrically constrained configuration in accordance with the present disclosure.

DETAILED DESCRIPTION OF THE PREFERRED EMBODIMENTS

Figure 1:
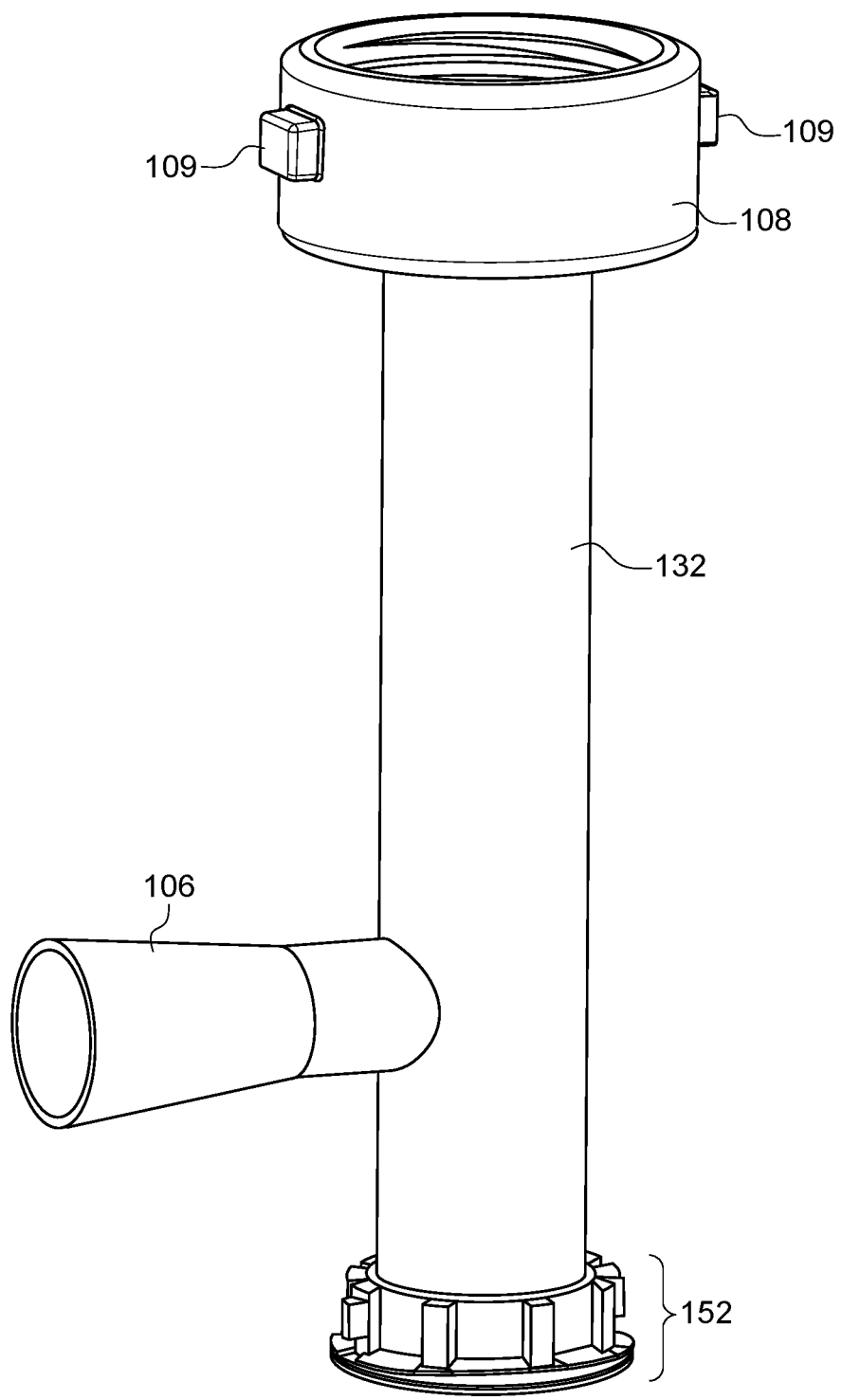
FIG. 1 is a perspective view of a tubular graft, hemostatic coupling and seating assembly in accordance with the present disclosure.

For purposes of clarity, the following terms used in this patent application will have the following meanings:

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising." "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

When an element or layer is referred to as being "on," "engaged," "connected," or "coupled" to or with another element, it may be directly on, engaged, connected or coupled to the other element or layer, or intervening elements or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at +10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The terms "proximal" or "distal" are intended to be relative positional references and are used with reference either to a direction of blood flow relative to a device or device component or with reference to a longitudinal axis of a device or device component. For example, with reference to the tubular prosthetic graft, the proximal end of the graft is the end in which blood flows into the graft, whereas the distal end of the graft is the end in which blood flows out of the graft. As an alternative example, the proximal end of the working chamber is the end furthest from the blood vessel being worked on and the distal end of the working chamber is the end closest to the blood vessel being worked on.

The term "saddle-shape" when used in connection with an element is intended to mean a generally hyperbolic paraboloid structure.

The term "graft" is intended to refer to any type of polymeric, biological, composite or metal tubular structure.

This detailed description of exemplary embodiments makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

In various embodiments and with reference to the Figures, a graft attachment system 100, including a tubular graft 132, flanged stent 160, and associated tools are provided. Hereinafter the graft connection system 100 will be referred to as "system 100." System 100 is configured, among other functions, to enable a practitioner to quickly and easily install a ventricular assist device ("VAD") in a patient, according to various embodiments. The system 100 and method 200 provides various benefits over conventional LVAD installation techniques, including, without limitation, decreased surgical times, reducing or perhaps even eliminating the time the patient is on cardiopulmonary bypass, increased ease and reproducibility of the installation, a decrease in bleeding, and a decrease in costs. While numerous details and embodiments are provided herein pertaining to the system 100 and its associated method being utilized to install a LVAD into a patient, the principles of the system 100 and the steps of the method may be applied to other surgical procedures and applications, including, for example and without limitation, other end-to-side anastomoses of grafts to anatomical structures in a body.

The tubular graft assembly is generally configured to enable a practitioner to quickly and easily make an end-to-side connection between a graft conduit and a hollow cardiovascular vessel (e.g., an artery), according to various embodiments. In various embodiments, the tubular graft assembly, in conjunction with the associated tools and method steps described below, is not necessarily intended to eliminate the use of cardiopulmonary bypass for VAD installation procedures, though certain surgeons may choose to attempt off-bypass implantation using these disclosed concepts.

Figure 22:
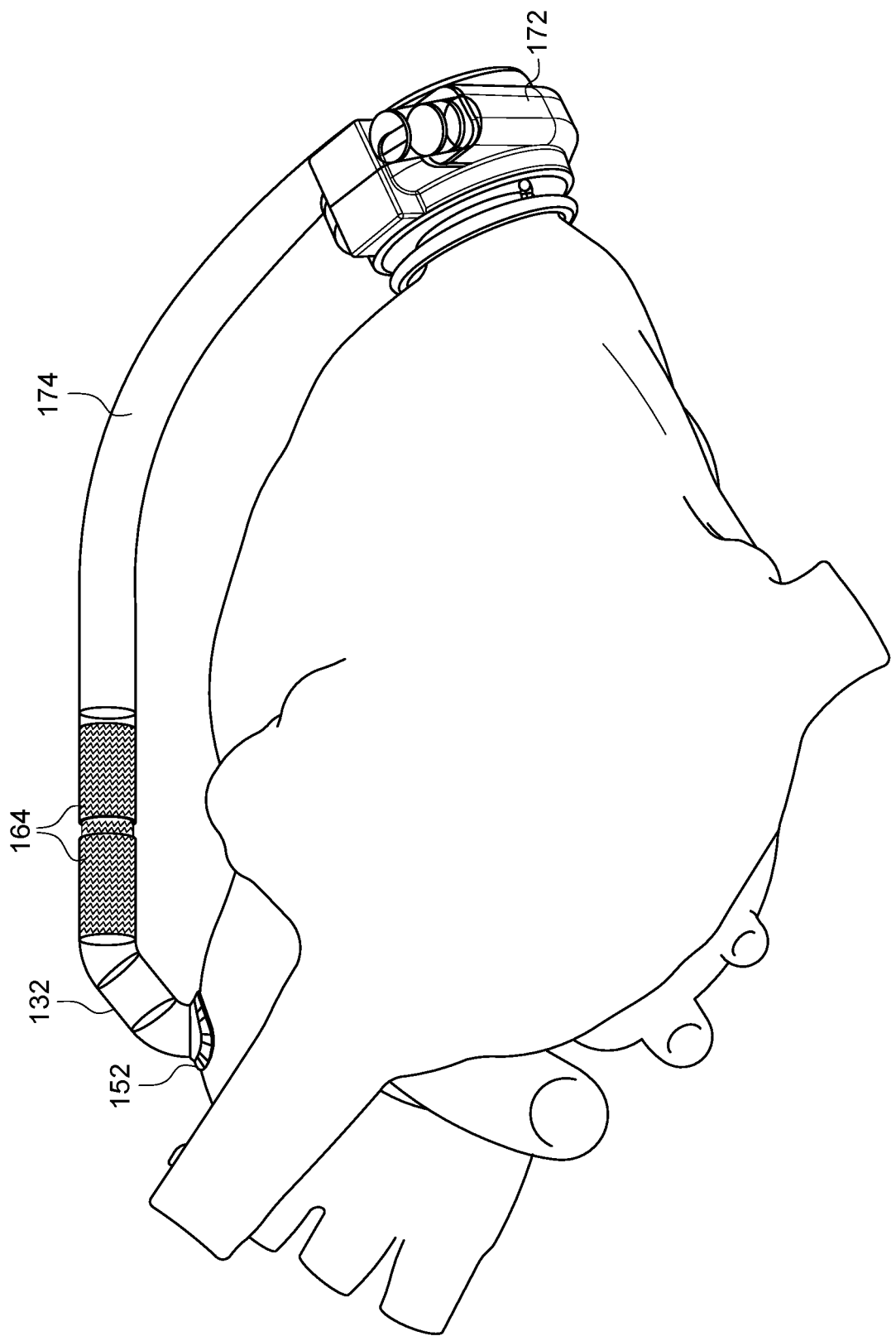
FIG. 22 is a perspective view illustrating a fully expanded end-to-end coupling joining the LVAD conduit with the tubular graft in accordance with the present invention showing a VAD, a VAD conduit and a heart for illustrative purposes.
Figure 23:
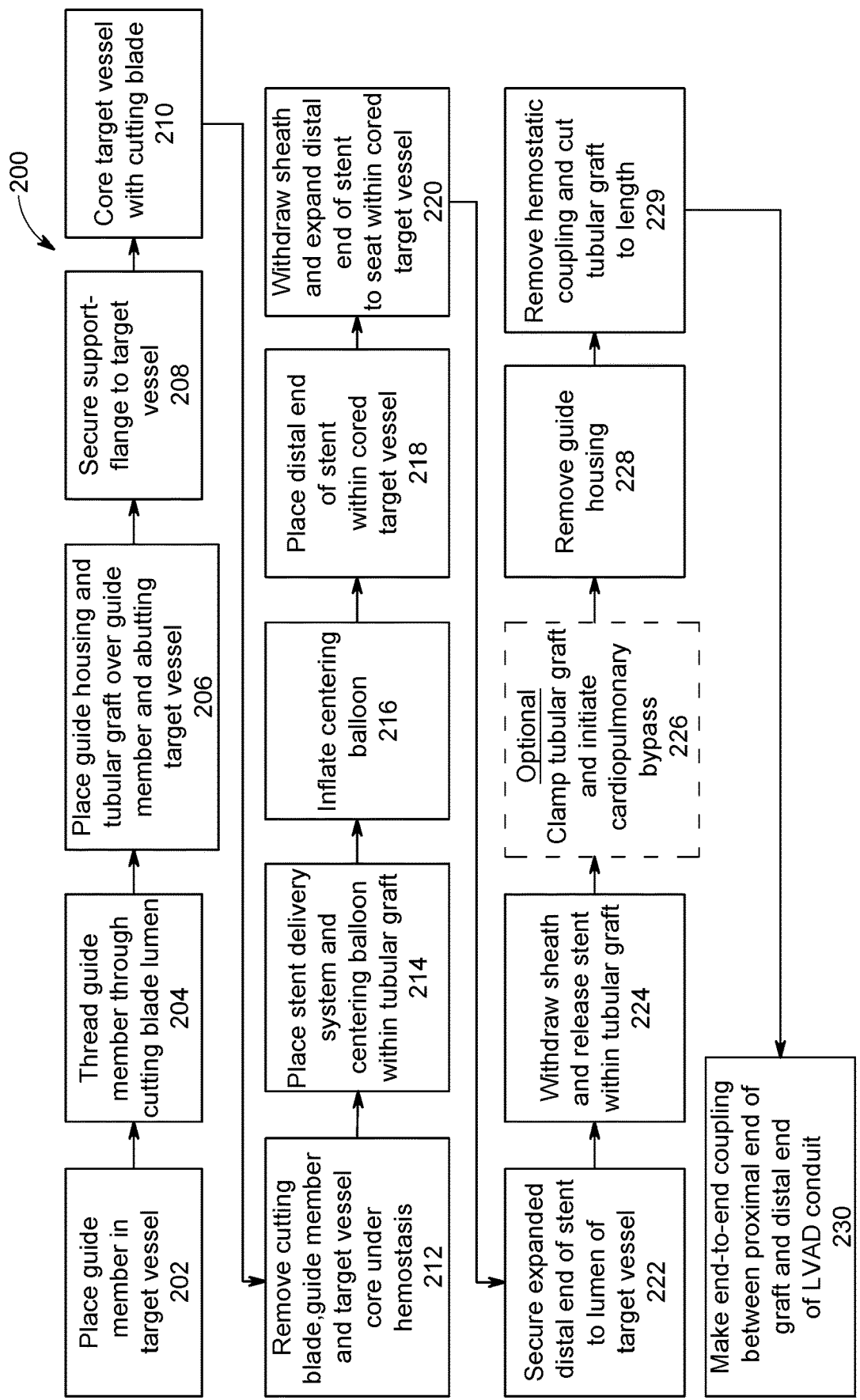
FIG. 23 is a flowchart diagrammatically illustrating the method of making an end-to-side attachment of the graft to the blood vessel or anatomical structure and an end-to-end attachment of the graft to the LVAD output conduit in accordance with the present disclosure.

Details and embodiments are provided herein pertaining to the use of a graft attachment system 100 as shown in FIGS. 1-22, including, its component parts, and a graft attachment method 200 as shown in FIG. 23, all of which are useful in VAD implantation. It will be understood and appreciated by those skilled in the art that the graft attachment system 100 and method 200 may equally have utility in other end-to-side connections within a body. That is, the provided disclosure generally relates to one or more methods, devices, assemblies, and systems for making connections with and/or between cardiovascular tissue, such as cardiovascular vessels, e.g., arteries or veins, or other anatomical structures requiring shunting or bypass, including, for example and without limitation, gastrointestinal, lymphatic, biliary or urinary structures. For example, the disclosure provides one or more methods, devices, assemblies, and systems that may be utilized for end-to-side connections and/or end-to-end connections between grafts and cardiovascular or other anatomic structures. Thus, the scope of the present disclosure is not necessarily limited to VAD installation applications.

The following described variants of system 100 and method 200 are set forth with reference to the accompanying Figures and describe the elements, components, and method steps of the using system 100 and employing method 200.

As shown in FIG. 22, in joining a LVAD device, the output of the LVAD pump 172 is coupled to the aorta via a LVAD conduit 174, coupled by the end-to-end connector 164 with the proximal end of tubular graft 132, and an end-to-side anastomosis between a distal end of the tubular graft 132 and the aorta. In this manner, blood existing the LVAD pump 172 is conveyed directly to the aorta.

Generally, the system 100 of the present invention includes a tubular graft 132 that is joined in an end-to-side fashion with a blood vessel. Tubular graft 132 is first secured to an outer wall surface of the blood vessel and then an opening in the blood vessel is created. The opening or stoma in the wall of the blood vessel may be made by introducing a cutting tool through a central lumen of the tubular graft 132 and cutting an opening or stoma in the wall of the blood vessel under hemostasis. Once the blood vessel wall opening is made and the blood vessel lumen is exposed, the cutting tool and excised wall tissue is removed through the central lumen of the tubular graft and a flanged stent 160 is introduced through the central lumen of the tubular graft 132 and delivered at a distal end of the tubular graft 132 and passes through and into the stoma and engages the luminal wall surface of the blood vessel, bearing against the distal end of the tubular graft 132. Once the distal end of the tubular graft 132 and the flanged stent 160 are secured, the proximal end of the tubular graft 132 is then coupled to the LVAD conduit in an end-to-end fashion, thereby completing the LVAD coupling to the blood vessel.

Figure 2:
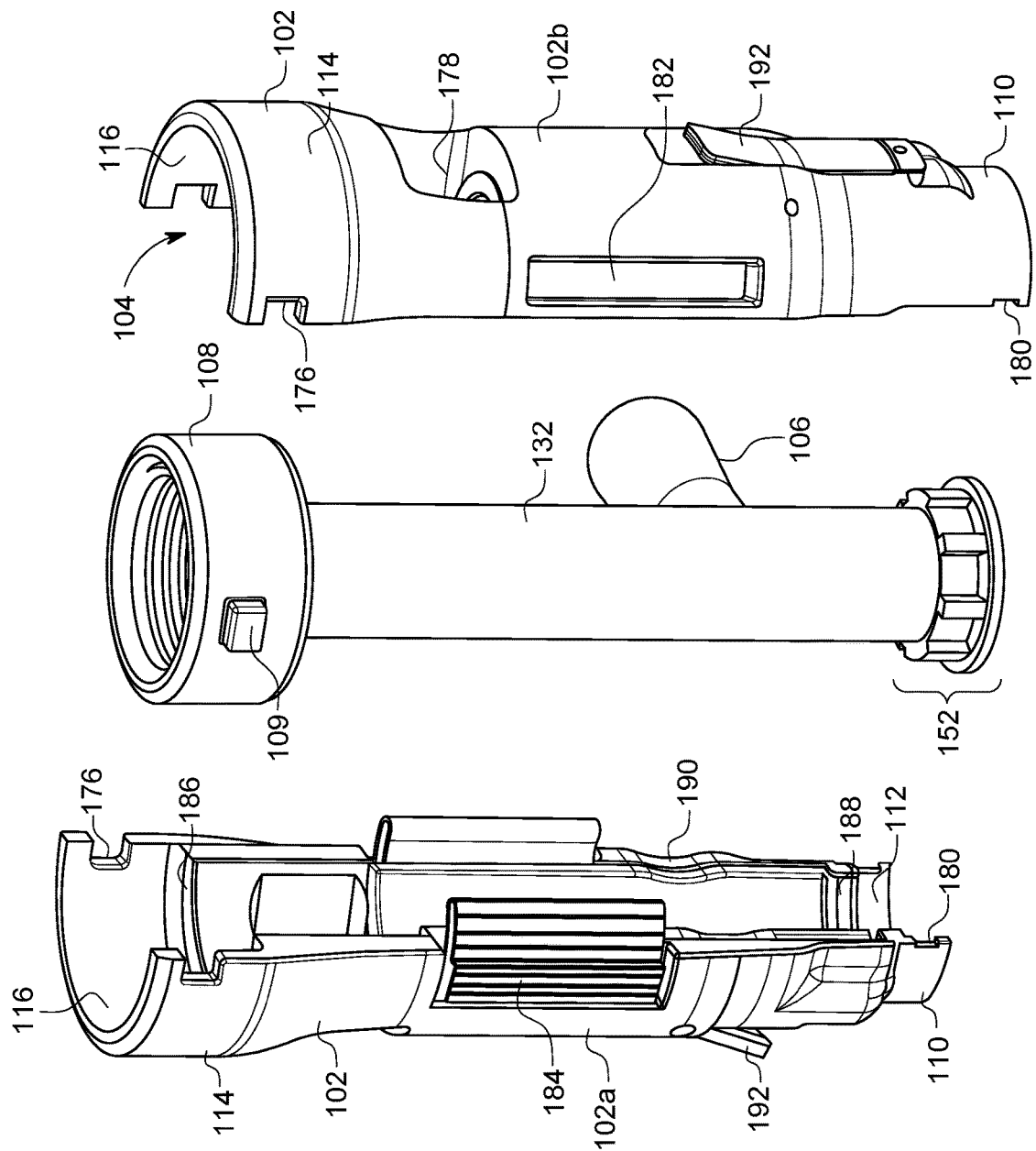
FIG. 2 is an exploded perspective view of the tubular graft and a graft housing in accordance with the present disclosure.
Figure 3A:
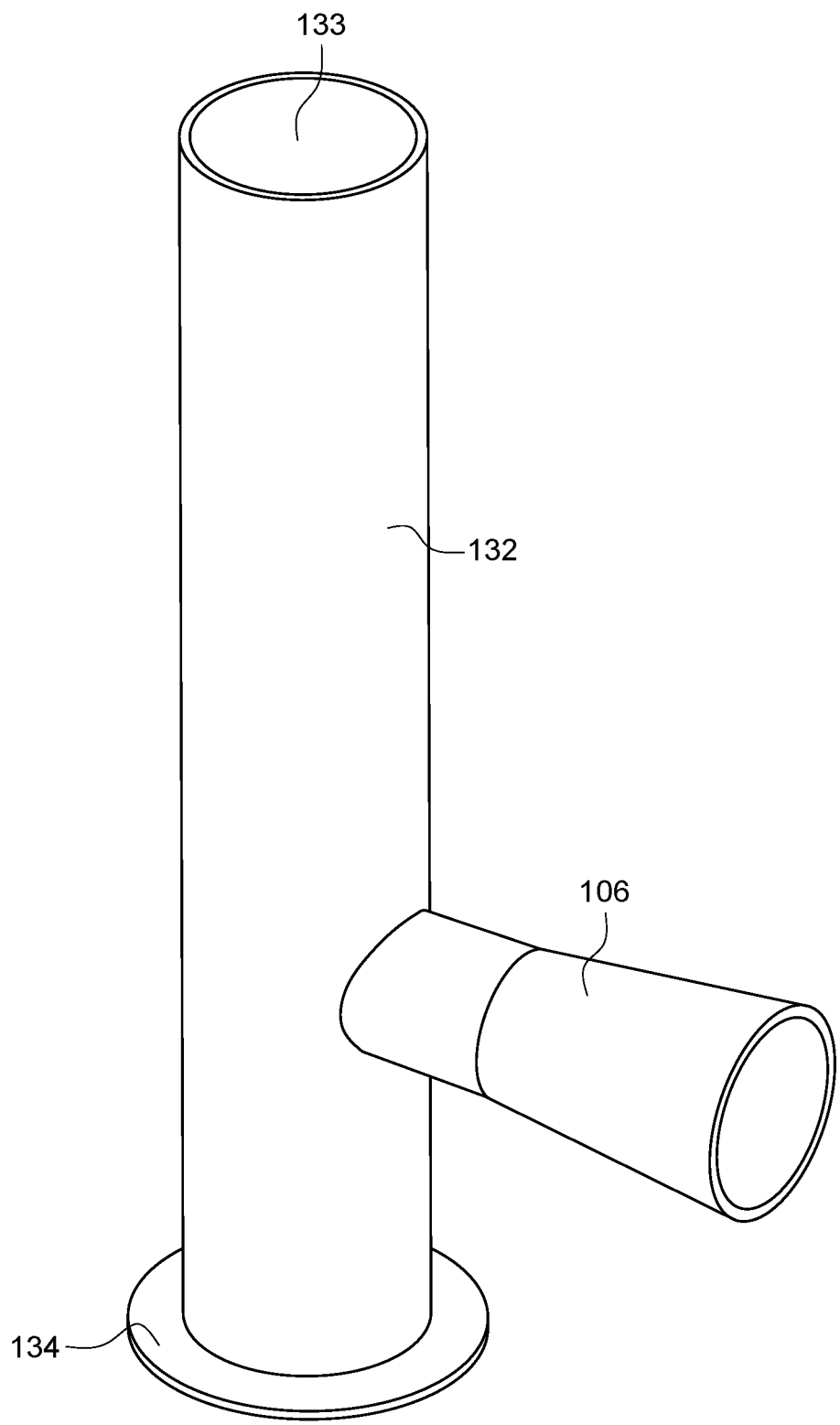
FIG. 3A is a perspective view of the tubular graft in accordance with the present disclosure.
Figure 3B:
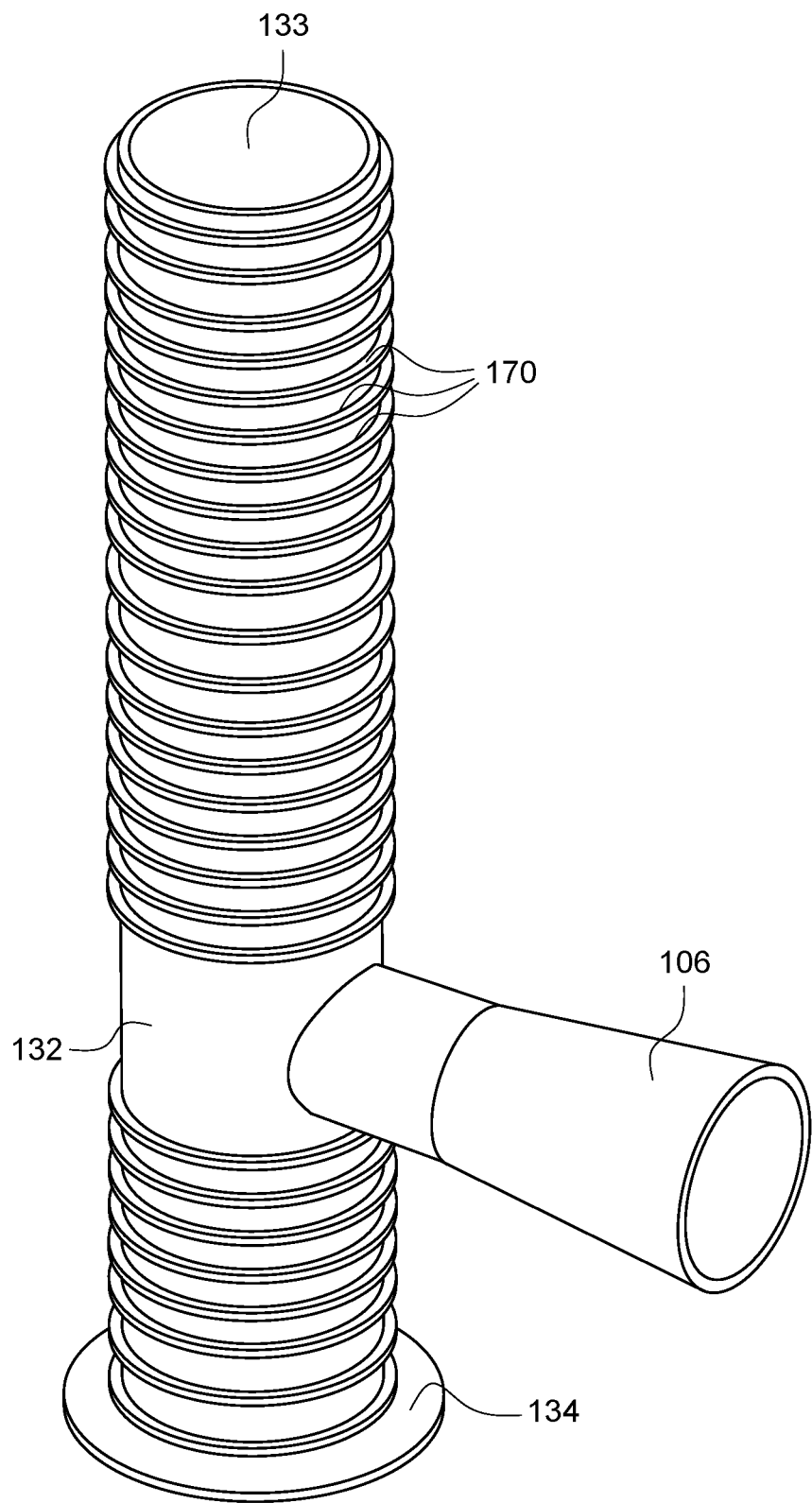
FIG. 3B is a perspective view of an alternative variant of the tubular graft in accordance with the present disclosure.

FIGS. 1-3B illustrate the tubular graft 132 of the present invention. To accomplish coupling of the LVAD conduit 174 (shown in FIG. 22) to the aorta, in accordance with one embodiment of the present invention there is provided a tubular graft 132 having a tubular graft lumen 133 and a graft skirt 134 at its distal end configured for end-to-side anastomosis with the aorta and a proximal end configured for end-to-end coupling with the LVAD conduit 174. In accordance with a second embodiment of the present invention the tubular graft 132 has a relatively longer proximal tubular graft portion that couples, at its proximal end, directly to the LVAD pump 172 and is has a graft skirt 134 at its distal end for end-to-side anastomosis with the aorta. In essence, the two embodiments are identical in general configuration, except that the first embodiment has a relatively shorter length proximal tube section and requires connection to the LVAD conduit 174 to span a distance between LVAD pump 172 and the aorta, whereas the second embodiment has a relatively longer length proximal tube portion and functions as both the LVAD conduit 174 and the end-to-side anastomosis at the aorta in a unitary tubular structure. As is shown in FIGS. 3A and 3B, the graft skirt 134 is a radially extending section of the tubular graft 132. While the graft skirt 134 may be integral and unitary with the tubular graft 132, i.e., without there being a seam or weld, the graft skirt 134 may also be a separate component extending radially outward from the tubular graft 132. The graft skirt 134 may have a generally planar shape or may have a generally saddle shape either shape being conformable to substantially conform to a wall surface of a blood vessel or anatomical structure, particularly both the longitudinal and circumferential curvature of the ascending aorta. In either configuration, the graft skirt 134 has at least a substantial surface area that conforms to the wall surface of the blood vessel or other anatomical structure.

Tubular graft 132 may further include a reinforcing support structure 170 that is either a separate element, such as rings, ribs, helical windings, fenestrated structures or the like, that are joined about an external wall surface or at least partially embedded within the wall surface of the tubular graft 132. Such reinforcing support structure 170 may be made of polymer, such as fluorinated ethylene propylene ("FEP"), stent-like structures made of shape memory materials, stent-like rings, or similar structures. The reinforcing support structure may be positioned only on the tubular aspect of the tubular graft 132 or may be additionally provided on or in the graft skirt 134.

Figure 4A:
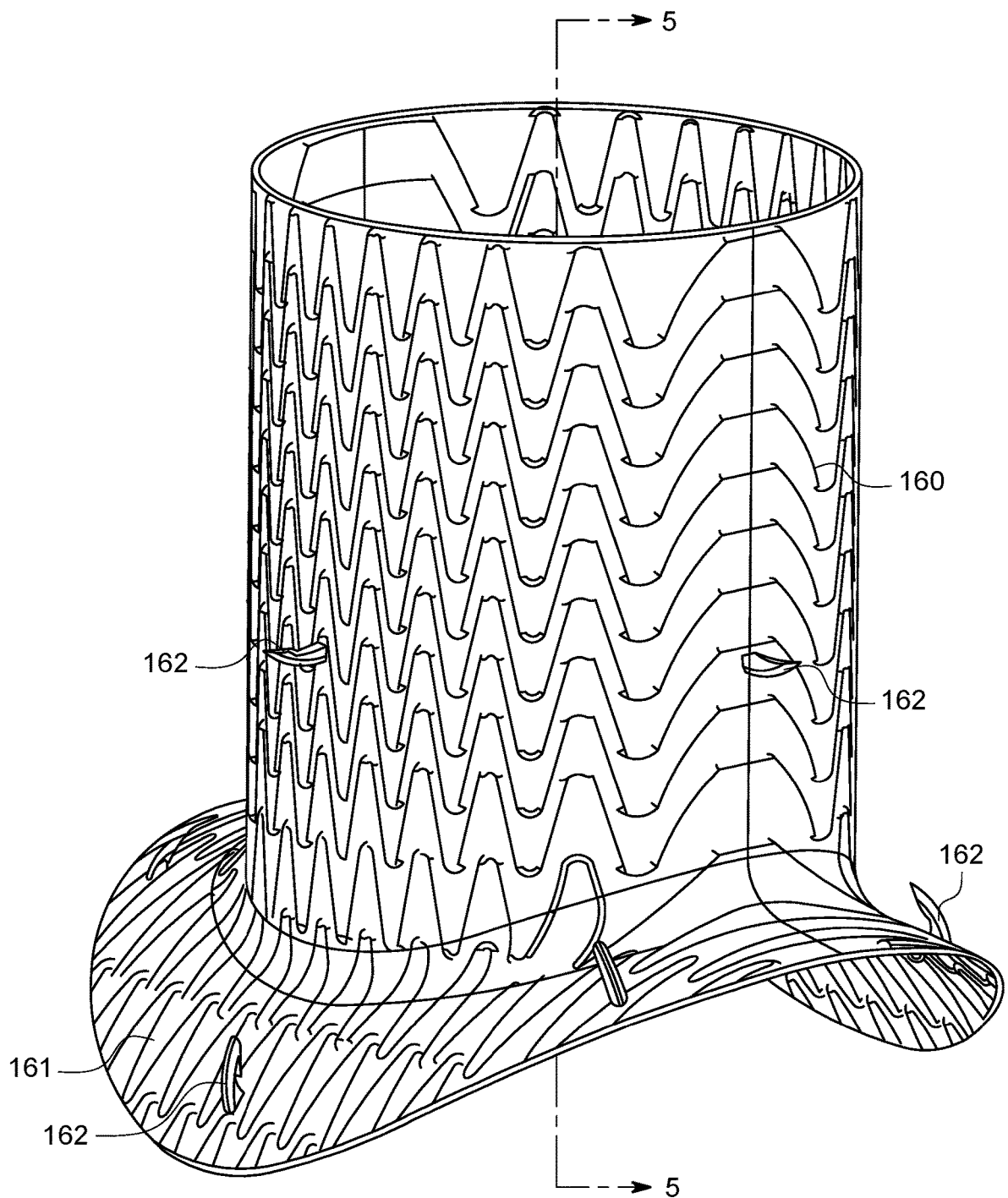
FIG. 4A is a perspective view of a stent in accordance with the present disclosure.
Figure 4B:
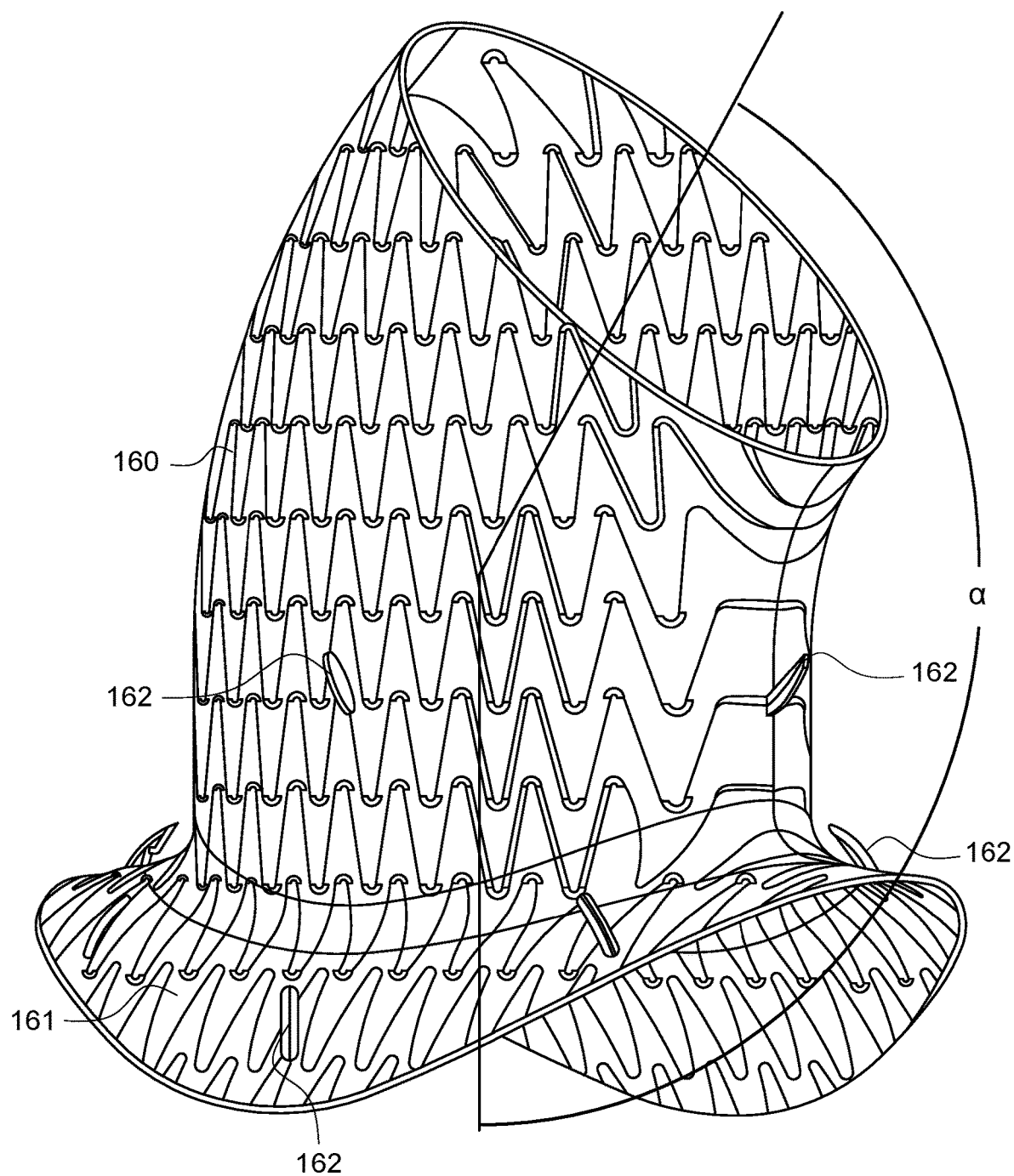
FIG. 4B is a perspective view of the stent in a bent configuration in accordance with the present disclosure.
Figure 5:
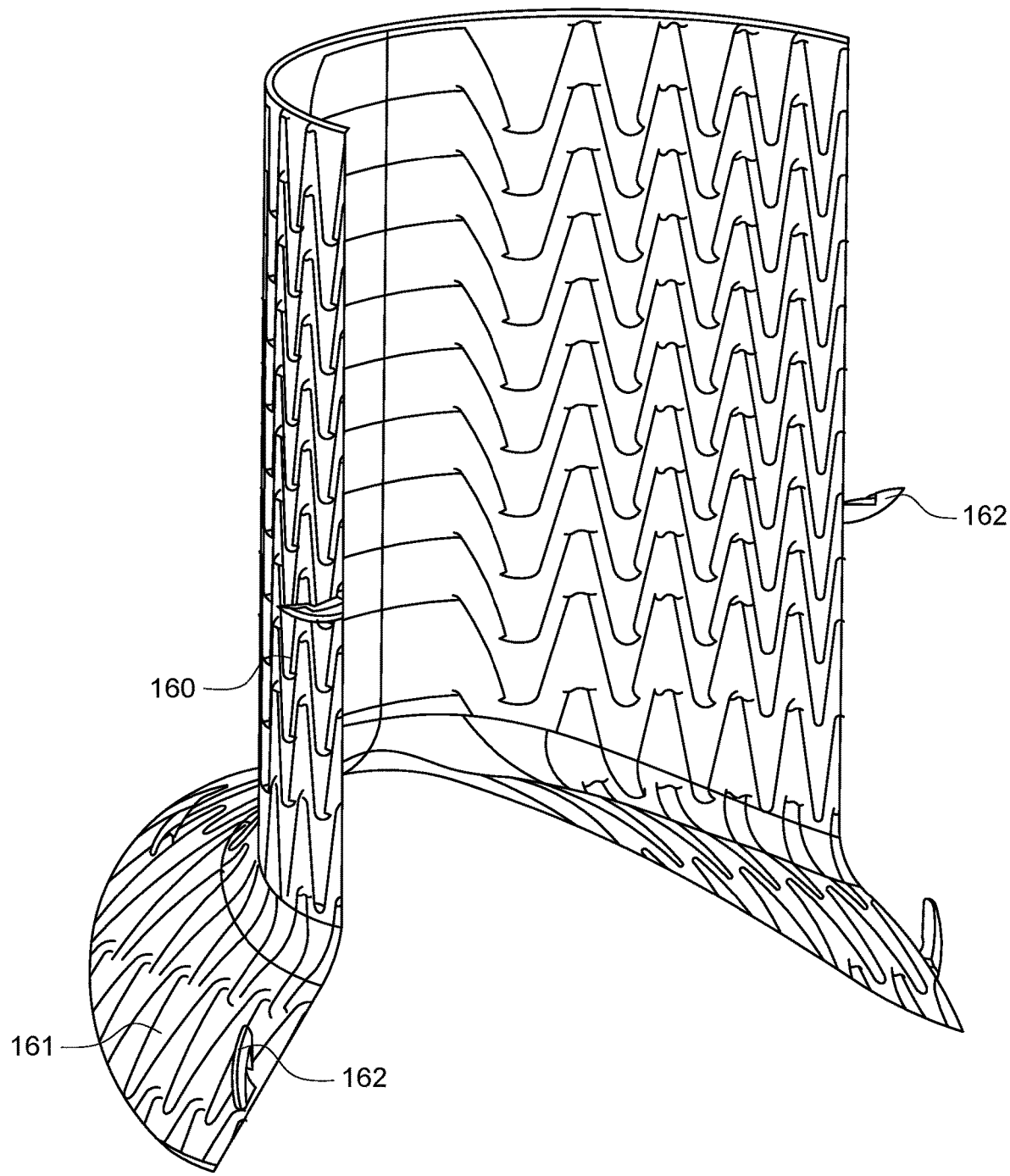
FIG. 5 is a perspective cross-sectional view taken along line 5-5 of FIG. 4A.
Figure 6B:
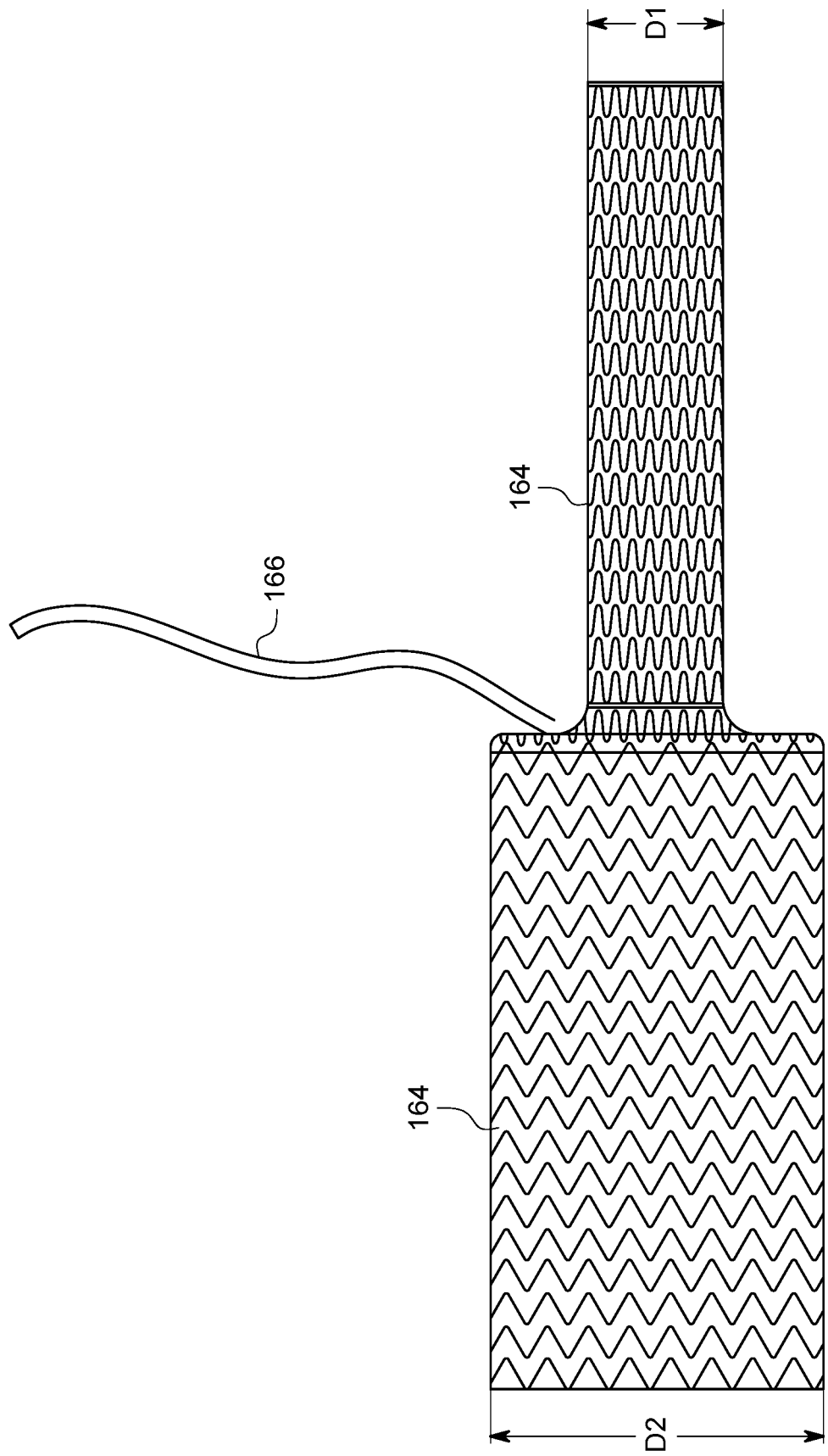
FIG. 6B is a side elevational view of the end-to-end connector in a partially diametrically constrained and partially diametrically expanded configuration in accordance with the present disclosure.
Figure 6C:
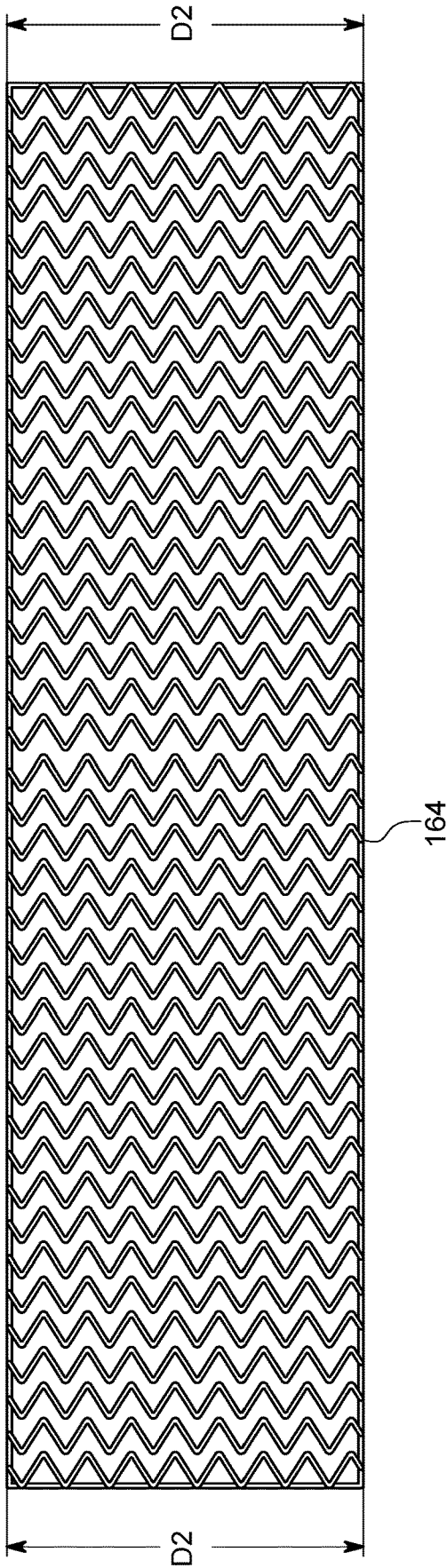
FIG. 6C is a side elevational view of the end-to-end graft in a full expanded configuration in accordance with the present disclosure.
Figure 7A:
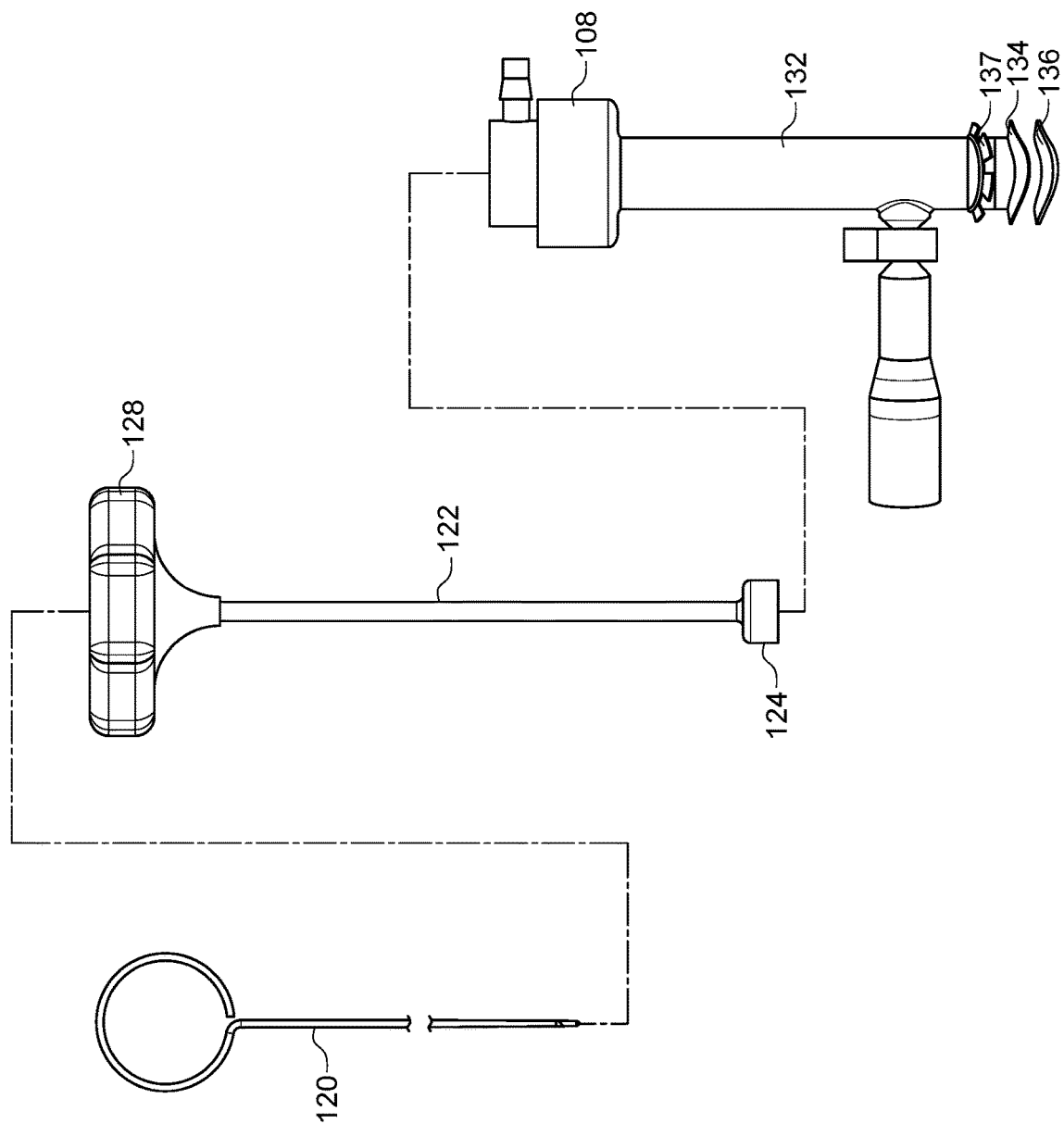
FIG. 7A is an exploded elevational view of a graft delivery system, without the graft housing assembly being shown for clarity, in accordance with the present disclosure.
Figure 7B:
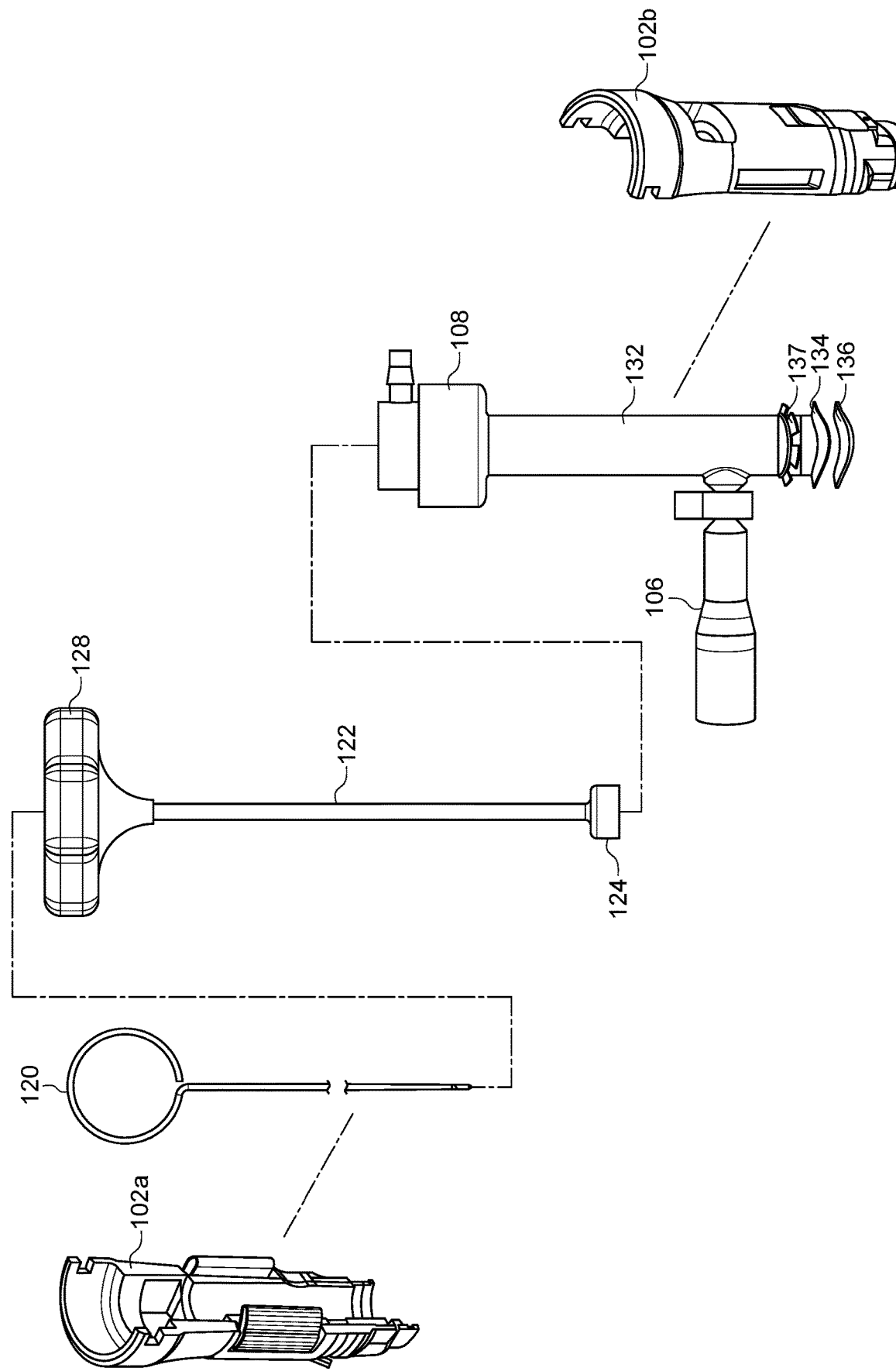
FIG. 7B is an exploded elevational view of a graft delivery system with the graft housing assembly shown in perspective view, in accordance with the present disclosure.
Figure 8:
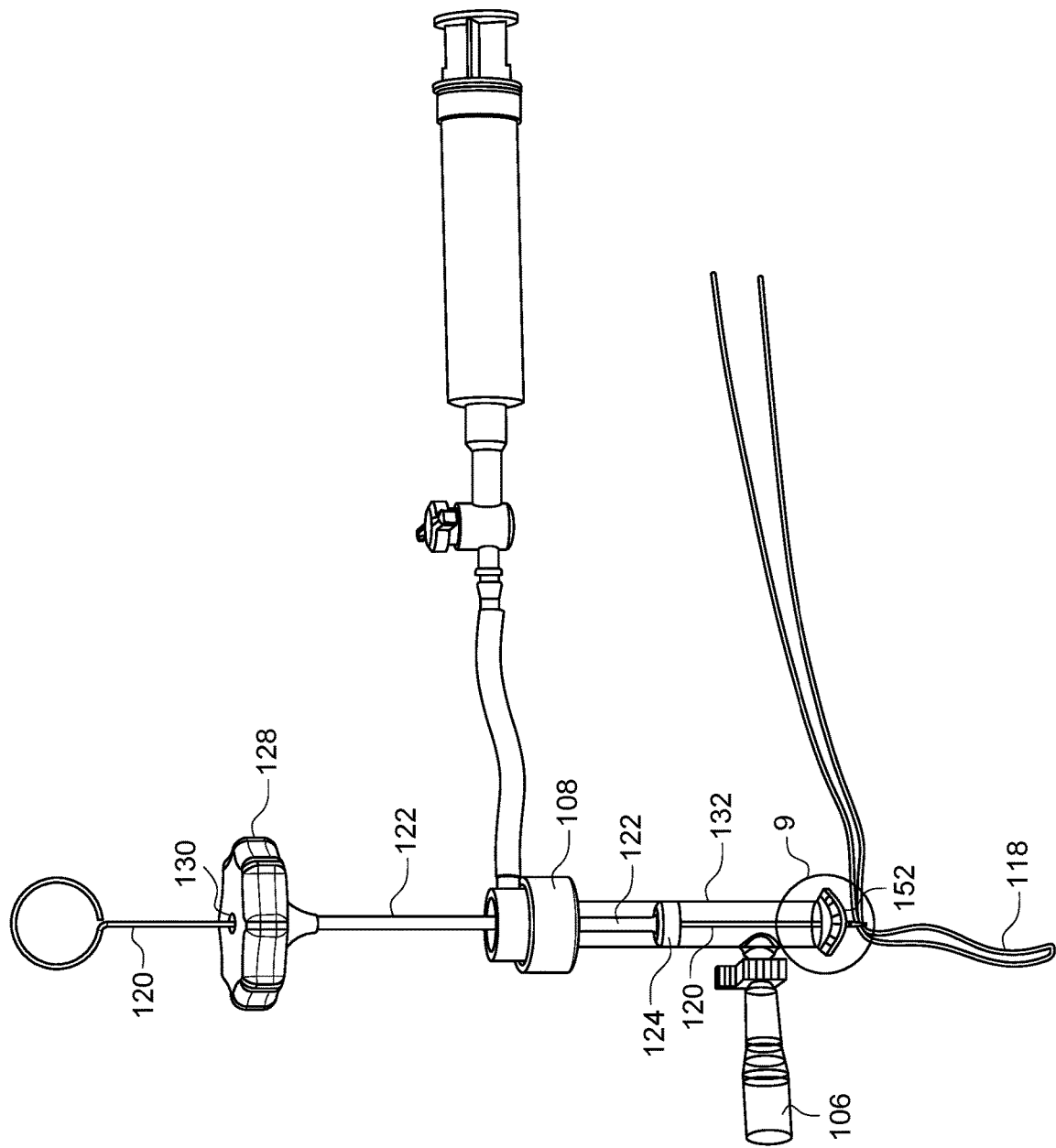
FIG. 8 is a perspective view of the graft delivery system configured for delivering the seating assembly and coring a blood vessel or anatomical structure in accordance with the present disclosure.
Figure 9A:
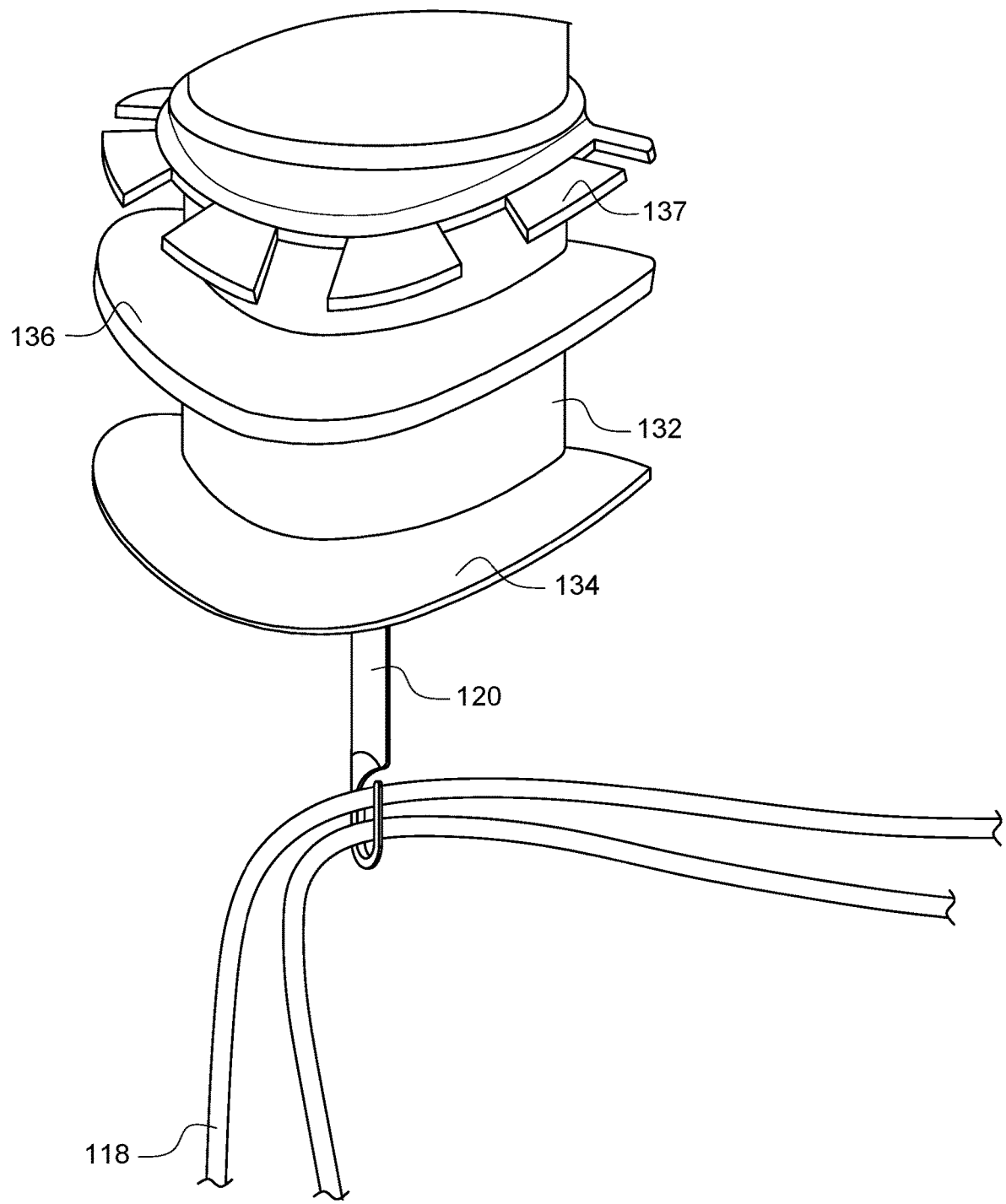
FIG. 9A is an enlarged view of a first arrangement of the seating assembly taken along section 9 of FIG. 8.
Figure 9B:
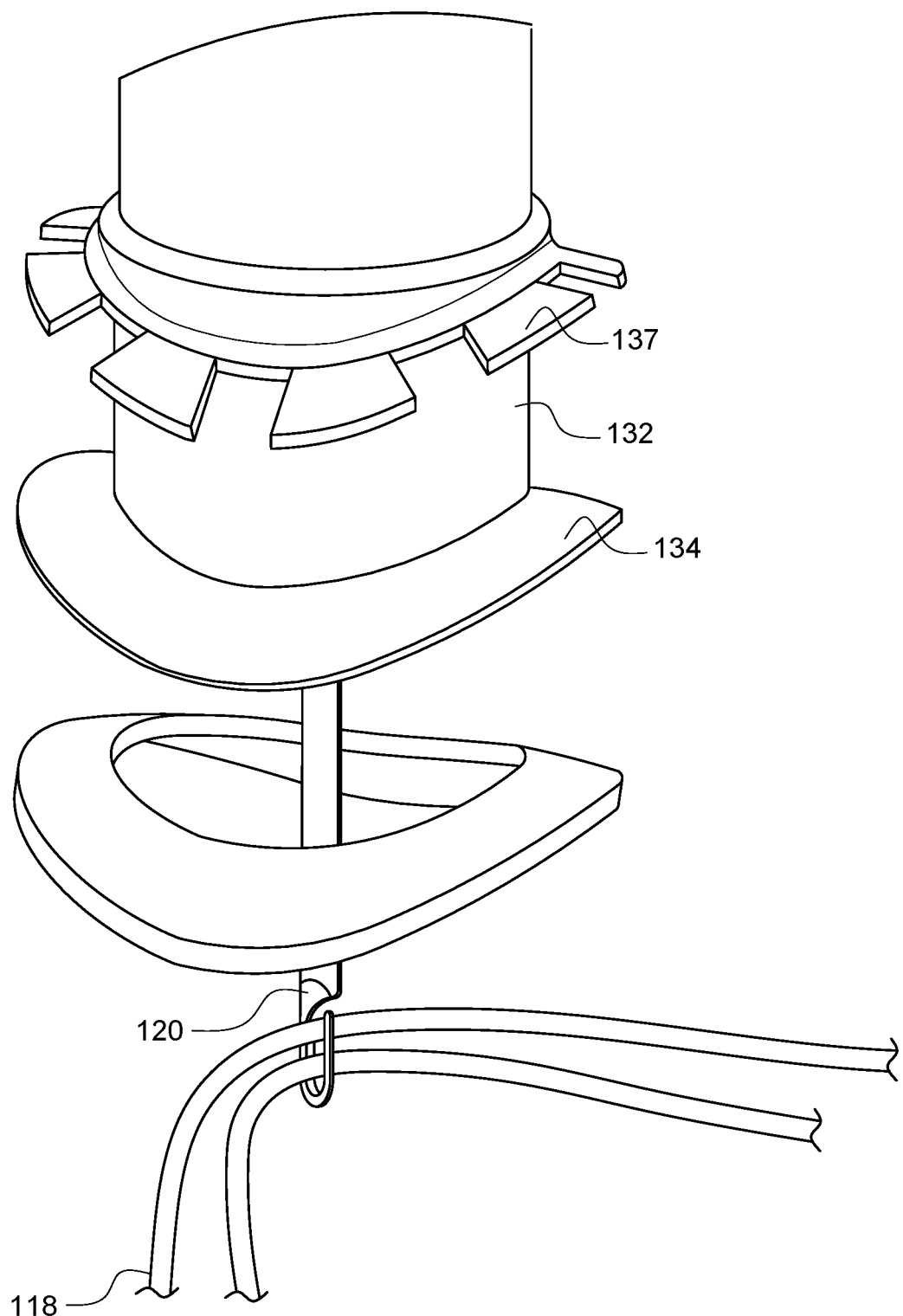
FIG. 9B is an enlarged view of a second arrangement of the seating assembly taken along section 9 of FIG. 8.
Figure 10A:
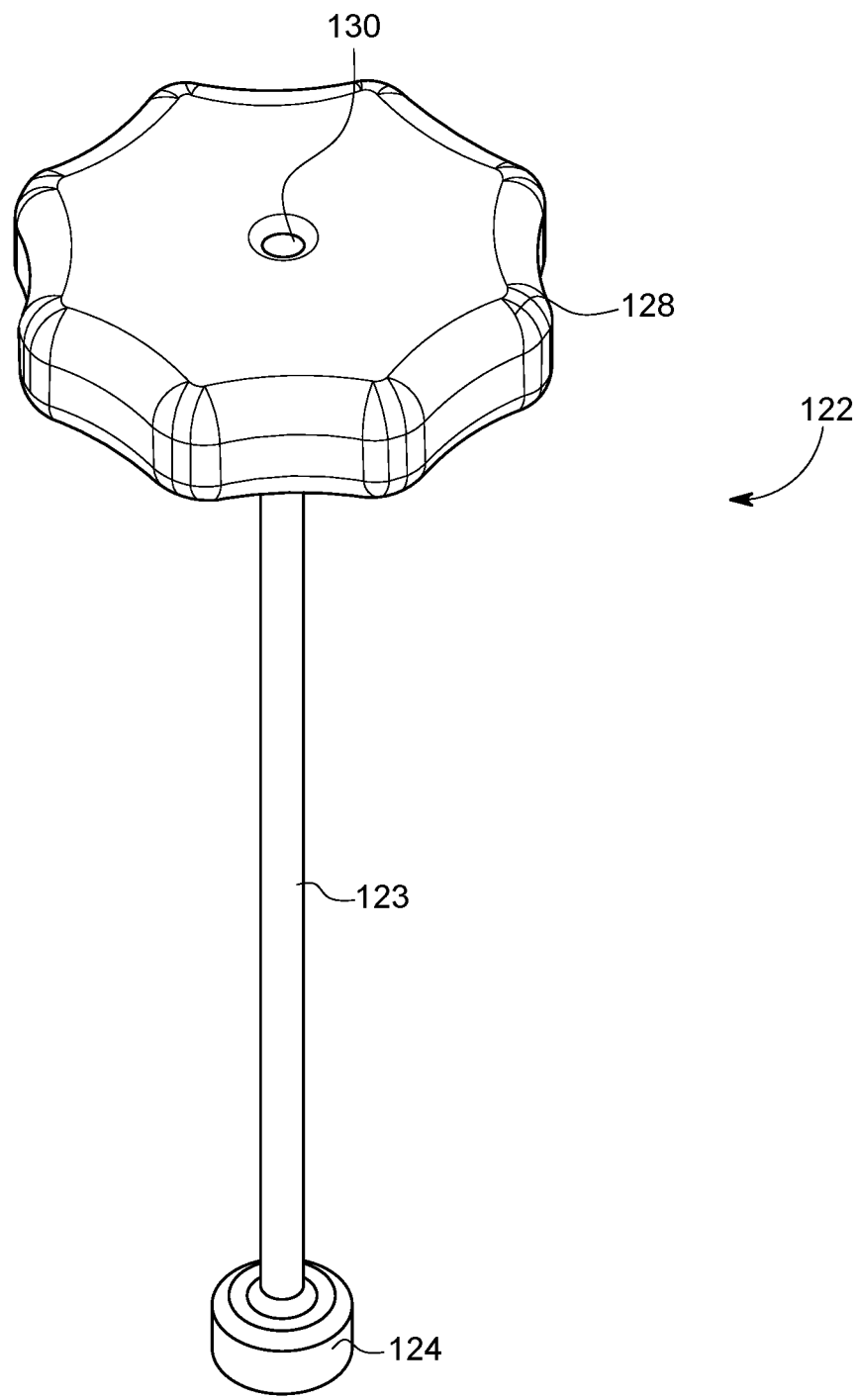
FIG. 10A is a first perspective view of a cutting tool in accordance with the present disclosure.
Figure 10B:
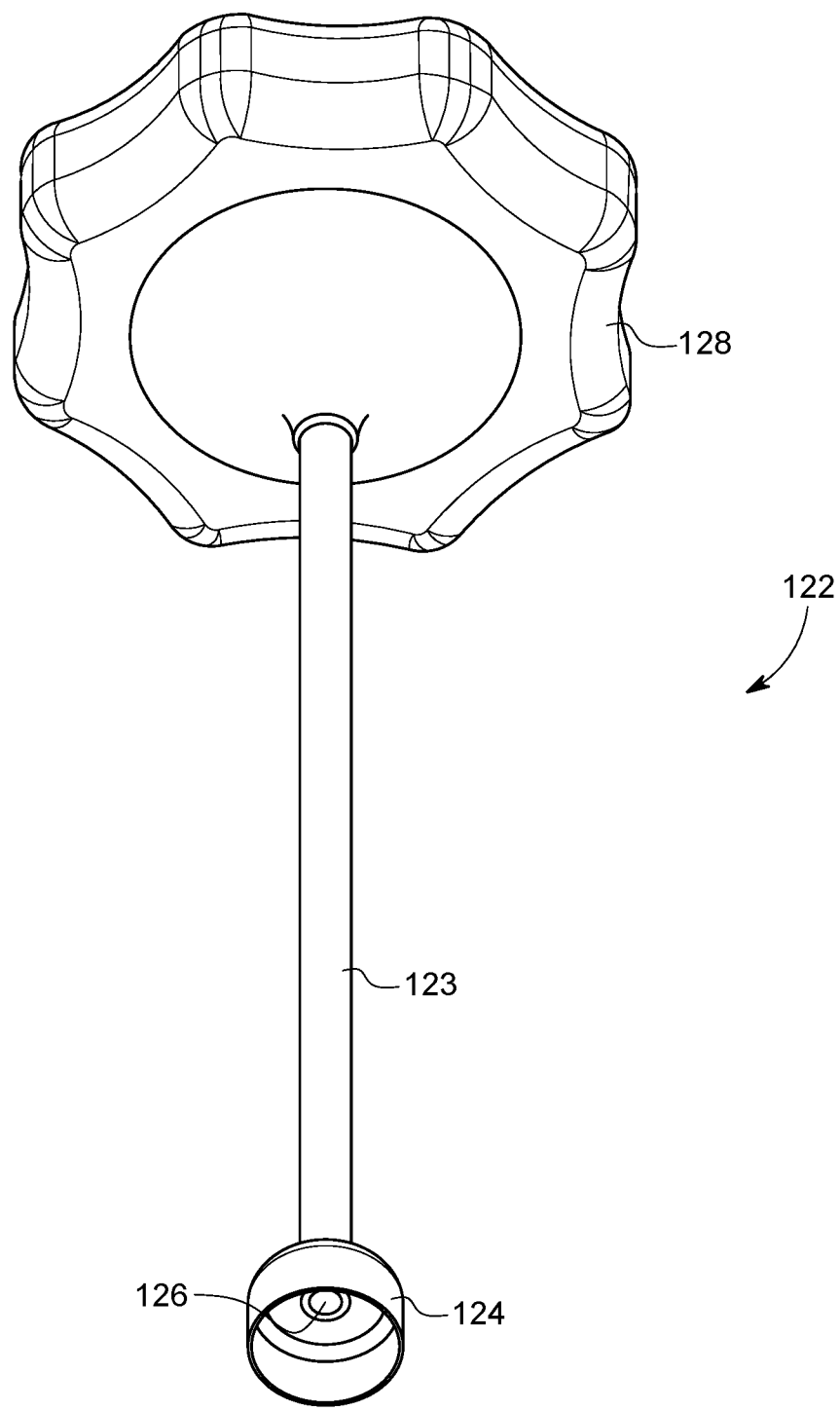
FIG. 10B is second perspective view of the cutting tool in accordance with the present invention.

FIGS. 4A-5 illustrate a flanged stent 160 that is employed to anchor tubular graft 132 and graft skirt 134 to the luminal wall surface of the blood vessel or anatomical structure. The flanged stent 160 may have a stent flange 161 at its distal end and the stent flange 161 or other portions of the flanged stent 160 may, optionally, have one or more barbs 162 that project outwardly from the flanged stent 160 or stent flange 161 to anchor into an opposing surface, such as the luminal wall of the blood vessel or anatomical structure and the distal end of tubular graft 132. Flanged stent 160 may optionally be configured to be capable of bending or deflecting to an angle α, where angle α is greater than 0 and up to 90 degrees from its central longitudinal axis. The flanged stent 160 may be a separate structure from tubular graft 132 or may be at least partially covered by or encapsulated by tubular graft 132. Further or alternatively, flanged stent 160 may be either fully or partially covered, on either or both the luminal or abluminal surfaces of the flanged stent 160, by a covering or graft separate from tubular graft 132.

The tubular graft 132 and/or the graft skirt 134 may also, in whole or in part, include a graft reinforcement 170 that serves as a support structure that either reinforces the tubular graft 132 and or the graft skirt 134. An example of an anchoring flanged support structure with a graft is illustrated in U.S. Pat. No. 6,652,578, which is hereby incorporated by reference in its entirety, teaching a cardiac valve stent having a stent-like support structure with an anchoring flange and a DACRON or expanded polytetrafluoroethylene ("PTFE") graft supported on either or both of a luminal or abluminal surface surfaces or the stent-like support structure. Tubular graft 132 may also be made of DACRON, PTFE or other suitable biocompatible polymeric material, biocompatible composite materials, biological material, biocompatible metals, or combinations thereof. PTFE grafts having an enlarged or flanged skirt for end-to-side anastomosis, and methods of making the same are exemplified by U.S. Pat. Nos. 6,190,590, 6,203,735 and/or 9,445,886, each of which is incorporated by reference.

Tubular graft 132 may, optionally, have a bypass connector 106 projecting radially outward from a wall of the tubular graft 132. When provided, bypass connector 106 may be a conduit that is in fluid communication with the central lumen of tubular graft 132. Preferably, bypass connector 106 is positioned to join with the wall of tubular graft 132 towards its distal end. Bypass connector 106 is removable from tubular graft 132 and the opening between bypass connector 106 and the central lumen of tubular graft 132 may be sealed with sutures, surgical staples or other known surgical methods of closing openings in grafts.

Figure 14A:
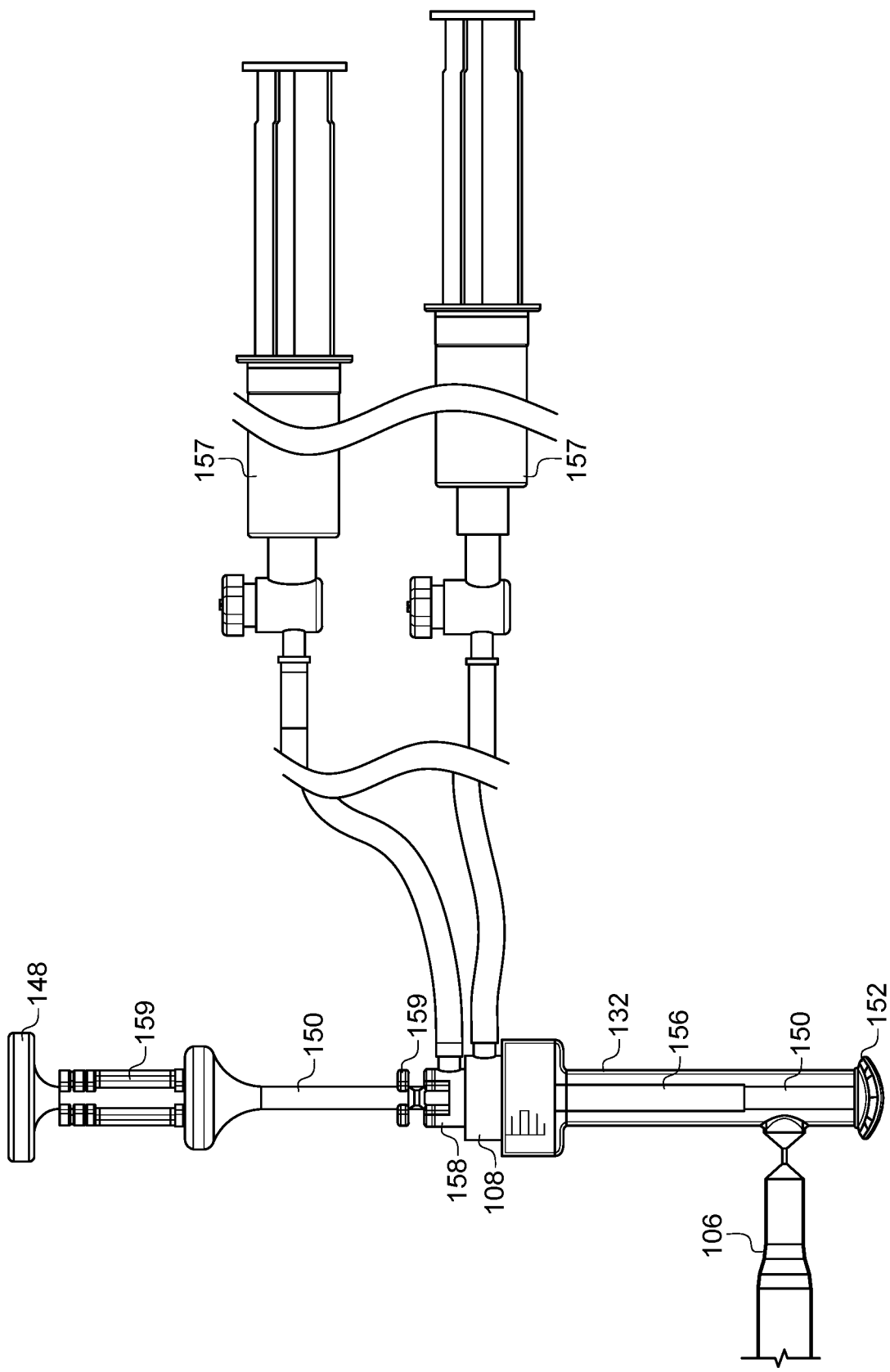
FIG. 14A is a side elevational view of the stent delivery system, tubular graft, hemostatic coupling and seating assembly in accordance with the present disclosure. The graft housing is not shown for clarity.
Figure 14B:
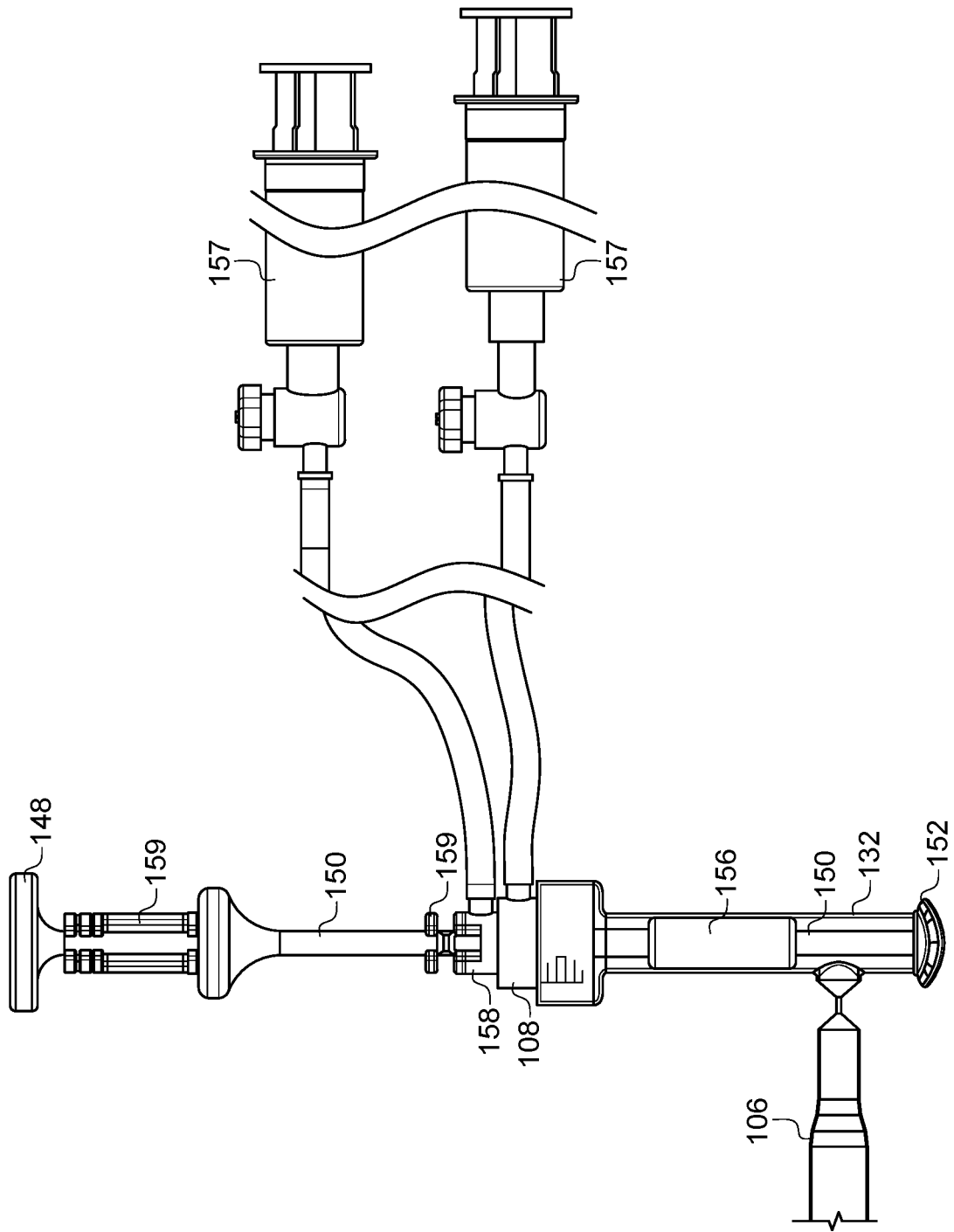
FIG. 14B is a side elevational view illustrating inflation of a centering balloon of the graft delivery system within the tubular graft in accordance with the present invention. The graft housing is not shown for clarity.

A hemostatic coupling 108 is coupled to a proximal end of the tubular graft 132 to provide a hemostatic seal that permits access through the hemostatic coupling 108 to the central lumen of tubular graft 132. Hemostatic coupling 108 also provides proximal support for tubular graft 132 when the tubular graft 132 is coupled to a graft housing 102. Depending upon its design, hemostatic coupling 108 may be actuatable by pressurizing or depressurizing an inflation fluid source 157, as illustrated in FIGS. 14A and 14B or may have other internal hemostatic seal configurations.

At a distal end of the tubular graft 132 there is provided a seating assembly 152. Seating assembly 152 consists generally of a staple ring 137 and a felt support ring 136 that cooperates with the graft skirt 134 to seat the tubular graft 132 at the anastomosis site. Staple ring 137 is concentrically positioned over the distal end of the tubular graft 132 proximal to the graft skirt 134. Felt support ring 136 may either be positioned concentrically around the tubular graft 132 and between the staple ring 137 and the graft skirt 134 or it may be positioned adjacent and distal to the graft skirt 134 such the felt support ring 136 abuts the wall surface of the blood vessel or other anatomical structure when the system 100 is attached thereto, or a felt support ring 136 may be positioned both proximal and distal the graft skirt 134. The felt support ring 136 acts as a seal that aids in absorbing blood, blood clotting and provides a tissue ingrowth scaffold for healing. Those skilled in the art will understand that felt support ring 136 may, alternatively, made of any biocompatible material that will seal the interface between the blood vessel and the graft skirt 134. Further, it will be understood that felt support ring 136 may be an adherent layer of a biocompatible sealing material disposed on either or both the proximal or distal surface(s) of the graft skirt 134.

A graft housing 102 is preferably and optionally provided. As depicted in FIG. 2, graft housing 102 preferably has at least two engageable sections that form a clamshell-like configuration. Alternatively graft housing 102 may be a unitary tubular member. A graft housing chamber 104 is defined within the graft housing 102 and extends from a proximal end 114 to a distal end 110 of the graft housing 102. At the proximal end 114 of graft housing 102, the graft housing 102 defines a proximal end opening 116, while at the distal end 110 of graft housing 102 the graft housing 102 defines a distal end opening 112. The tubular graft 132, hemostatic coupling 108 and the seating assembly 152 are contained within the housing chamber 104 of graft housing 102 for delivery of the tubular graft 132 and flanged stent 160 at the anastomosis site.

For purposes of clarity, the at least two removably coupled sections of the graft housing 102 will be referred to as first housing section 102A and second housing section 102B. Each of the first housing section 102A and second housing section 102B are substantially symmetrical. Each housing section 102A and 102B have a proximal detent 176 and a distal detent 180 at the proximal end 114 and distal end 110 of each of the housing sections 102A, 102B. The proximal detent 176 is configured to engage with a mating protuberance 109 on an outer peripheral surface of the hemostatic coupling 108. A proximal seat 186, which may comprise a circumferential ring, circumferential flange, or other seating projection, projects circumferentially inward from and in proximity to the proximal end of each of the first housing section 102A and second housing section 102B. When the graft housing 102 is assembled, proximal seat 186 abuts and supports a distal surface of the hemostatic coupling 108. Similarly, a distal seat 188, which also may comprise a circumferential ring, circumferential flange, or other seating projection, projects circumferentially inward from and in proximity to the distal end of each of the first housing section 102A and 102B. Like with proximal seat 186, distal seat 188 abuts and supports seating assembly 152 when the graft housing 102 is assembled. In this manner, the tubular graft 132 is supported within the graft housing chamber 104. The staple ring 137 may also have one or more distal protuberances (not shown) that removably engage with one or more of the distal detents 180 in each of housing sections 102A and 102B.

Each of the housing sections 102A and 102B further have a clamp opening 178 proximal to a mid-line of the length of graft housing 102 and passing through side wall surfaces of each of the housing sections 102A and 102B. Clamp openings 178 permit access for the surgeon to pass a surgical clamp, such as hemostats, through the clamp opening 178 to clamp off the tubular graft 132 when necessary without removing the graft housing 102. The first graft housing 102A further includes at least one snap or spring connector 184 each of which cooperates with an intermediate detent 182 in the side wall surface of second housing section 102B. As illustrated in FIG. 2, where two spring connectors 184 are provided, it is preferable that they be positioned 180 degrees from one another about the diameter of the graft housing.

Each of the housing sections 102A and 102B may have mating recesses 190 that when the housing sections 102A and 102B are joined a bypass port opening (not shown) is formed that accommodates the optional bypass connector 106 to pass there through and allow for removal of the graft housing 102 from the tubular graft 132 and bypass connector 106, if present.

Finally, each of the housing sections 102A and 102B may have an integrated staple firing mechanism activated by actuators 192 accessible from the outer wall surface of each of housing sections 102A and 102B. Actuators 192 will release springs contained within each housing section 102A and 102B. Each of the springs (not shown) bear on a following block that, in turn, bears upon a corresponding staple head 143 that drives the staple leg 145 into the wall of the blood vessel or anatomical tissue.

It will be appreciated that, in the foregoing configuration, the tubular graft 132 is longitudinally supported in graft housing chamber 104 and within the graft housing 102.

The optional bypass connector 106 is useful when cardiopulmonary bypass is required and avoids the need for central aortic or peripheral arterial cannulation. Venous cannulation may be accomplished by percutaneous or other method. In other embodiments in which cardiopulmonary bypass is not required or alternative arterial access is employed, the bypass connector 106 may be omitted from the tubular graft 132.

Turning now to FIGS. 7A-12, the seating assembly 152 and system 100 is illustrated. System 100 for delivery and affixation of tubular graft 132 to a blood vessel includes, as discussed above, the graft housing 102 and graft housing chamber 104 (both not shown for purposes of clarity). The tubular graft 132, hemostatic coupling 108, and seating assembly 152 are axially aligned such that a common working channel is provided through their central longitudinal axis. A cutting tool 122 is provided that has a handle 128 with a de-airing opening 130, a cutting tool conduit 123 extending from the handle 128, a cutting blade 124 at a distal end of the cutting tool conduit 123, and a cutting tool lumen 126 in the cutting tool conduit 123 that communicates between the cutting blade 124 and the de-airing opening 130. The cutting tool 122 may be passed through the hemostatic coupling 108 or may be pre-loaded by passing the cutting tool 122 with the handle 128 removed through the distal end of the tubular graft 132. The cutting blade 124 is preferably a circular blade having an inward bevel such that a cutting edge of the cutting blade 124 is on the inner circumferential surface of the cutting blade 124. In this manner, the cutting blade 124 is less likely to damage the luminal wall of the tubular graft 132 during operation.

The staple ring 137 may have a saddle flange 138 that is generally saddle-shaped with a curvature that conforms to the circumferential curvature of a blood vessel, particularly, the aorta. Alternatively the staple ring 137 may not have a saddle flange 138 or any appreciable flange whatsoever. FIGS. 16A-17B illustrate two exemplary variants of the staple ring 137 with and without the saddle flange 138.

Figure 11:
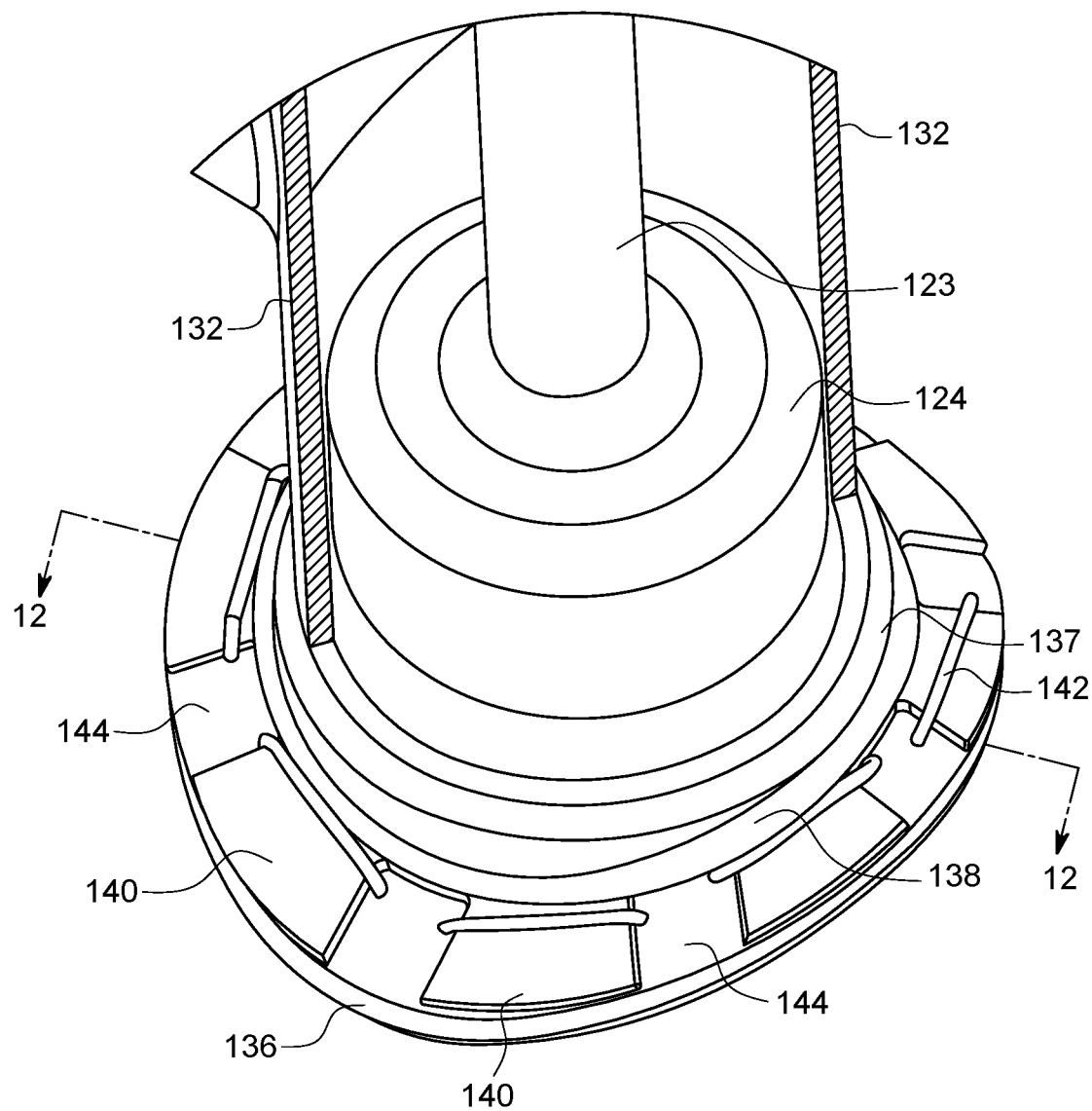
FIG. 11 is a top perspective partial cross-sectional view illustrating attachment of the seating assembly to a blood vessel and a cutting tool in accordance with the present disclosure.
Figure 12:
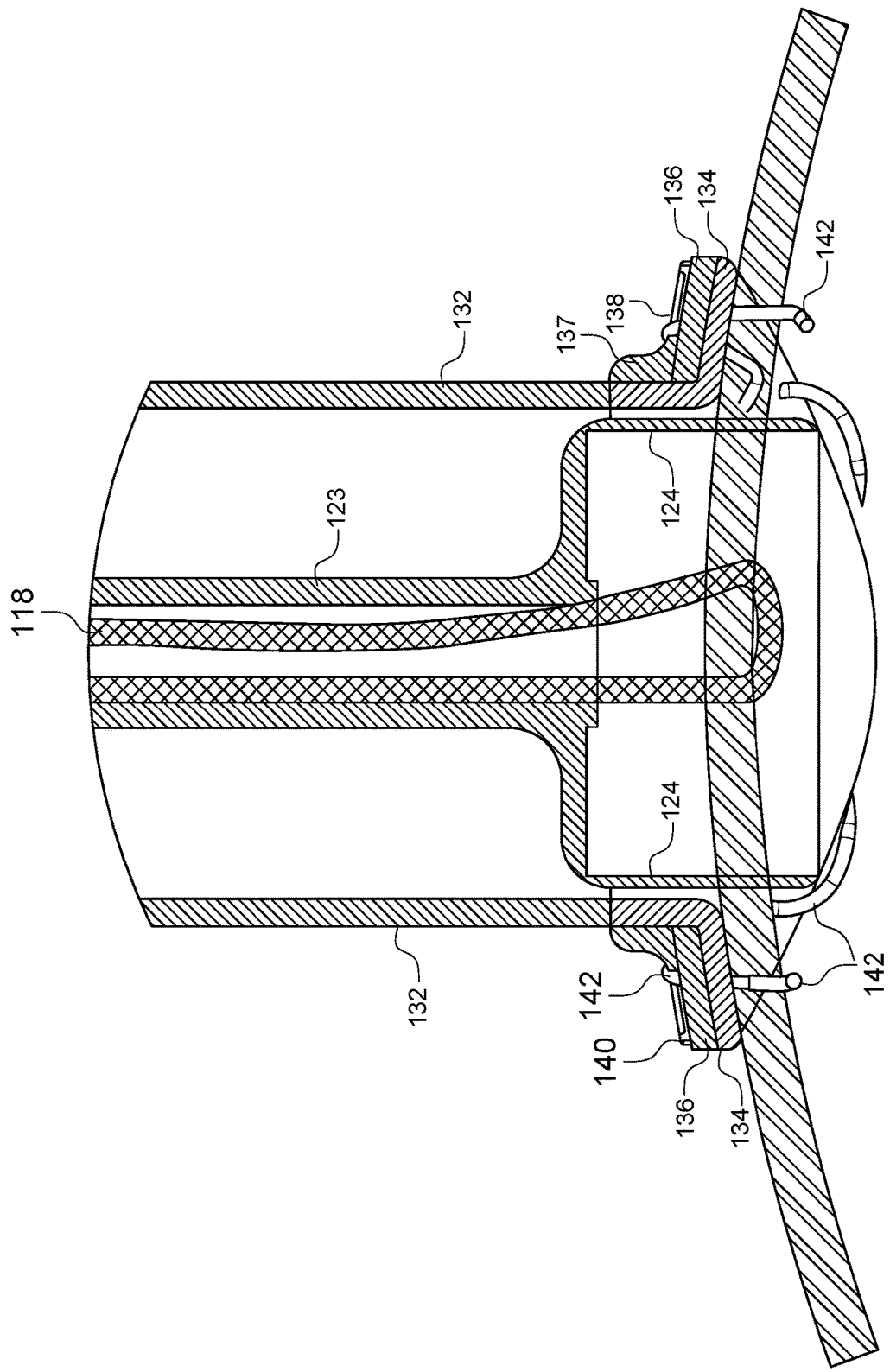
FIG. 12 is a cross-sectional view taken along line 12-12 of FIG. 11.

According to one embodiment of the staple ring 137, there is provided a saddle flange 138 that has a plurality of saddle flange segments 140 extending radially outward from the saddle flange 138. The plurality of saddle flange segments 140 are circumferentially spaced apart from each other thereby defining a plurality of radial slots 144. The saddle flange segments 140 aid in maintaining apposition between the saddle flange 138, the felt support ring 136 and the blood vessel or other anatomical structure. This embodiment of staple ring 137 is best illustrated in FIGS. 11 and 12.

According to another embodiment of the staple ring 137, as illustrated in FIGS. 16A-17B, the staple ring 137, either with or without the saddle flange 138, has a plurality of staple apertures 141 that pass through the staple ring 137. In accordance with this embodiment of the staple ring 137, the saddle flange segments 140 may or may not be present.

The staple ring 137 and saddle flange 138 are preferably made of a rigid or semi-rigid material capable of maintaining hemostasis with the vessel or anatomical structure to which it is joined, accept a compression force from the staples 142 and bear against the felt support ring 136 and graft skirt 134. Suitable materials for the staple ring 137 and saddle flange 138 include, for example, polyether ether ketone, commonly referred to as PEEK, PTFE, and titanium or other biocompatible metals compatible with the material used for the surgical staples 142.

Figure 13:
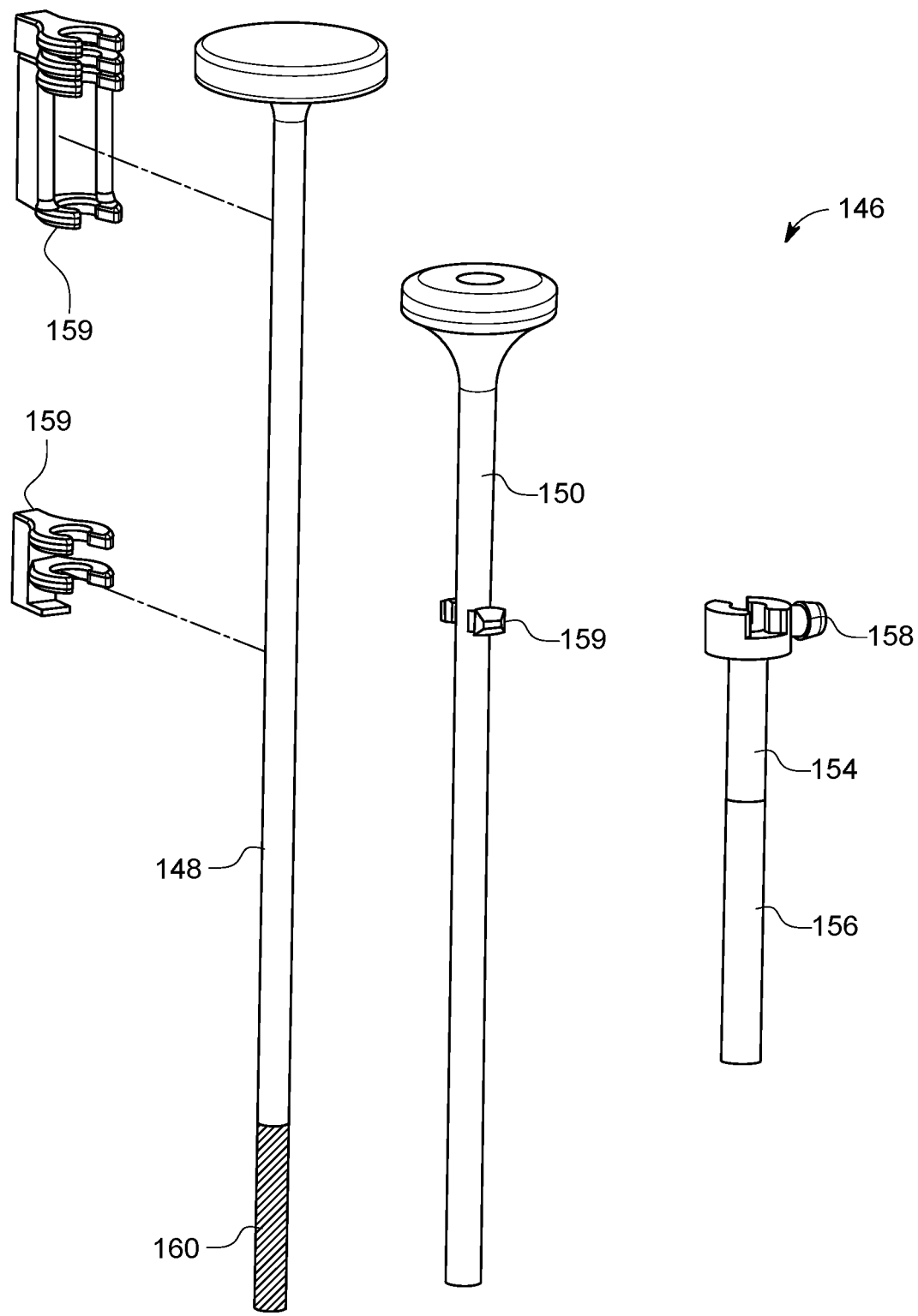
FIG. 13 is an exploded view of a stent delivery system in accordance with the present disclosure.

Finally, a stent delivery system 146 is provided as illustrated in FIG. 13. Stent delivery system 146 is used to deliver flanged stent 160 within the tubular graft 132 and secure the flanged stent 160 against the luminal wall of the blood vessel or anatomical structure and against the central lumen wall at the distal end of the tubular graft 132.

Stent delivery system 146 consists generally of a pusher 148 having the flanged stent 160 carried on the pusher 148 in a collapsed and constrained configuration, an inner delivery sheath 150 having a lumen into which the pusher 148 passes, an outer delivery sheath 154 that carries a centering balloon 156. The outer delivery sheath 154 has a lumen into which the inner delivery sheath 150 and the pusher 148 with flanged stent 160 passes. Outer delivery sheath 154 also has an inflation lumen in fluid flow communication with a centering balloon inflation port 158. The centering balloon 156 is inflated and deflated by pressurizing and depressurizing fluid from an inflation fluid source 157, such as a syringe. The inflation lumen of the outer delivery sheath 154 terminates on a distal end in a first inflation port communicating with the centering balloon 156 and terminates on a proximal end in a second inflation port and an inflation connector, such as a valved Luer fitting, that removably couples to an inflation fluid source, such as a syringe. Pusher 148 is concentrically positioned and reciprocally movable within the inner delivery sheath 150 which also constrains the flanged stent 160 carried on the pusher 148. Pusher 148 and inner delivery sheath 150 are, in turn, concentrically positioned and reciprocally movable within the outer delivery sheath 154. A plurality of stop collars 159 may be engaged on the pusher 148 or the inner delivery sheath 150, or both, to delimit movement of the pusher 148 and the inner delivery sheath 150 relative to each other or to the outer delivery sheath.

In operation, a guide member 118, such as a suture or endoscopic biopsy forceps, is placed on a desired position in the vessel or other anatomical structure to demarcate an approximate center point for the end-to-side anastomosis of the tubular graft 132. The graft housing 102, tubular graft 132, and seating assembly 152, including staple ring 137, saddle flange 138, if present, felt support ring 136, and graft skirt 134 are passed over the guide member 118 and positioned in approximation with the vessel or anatomical structure. If the cutting tool 122 is preloaded within the tubular graft 132, and a guide suture is used as guide member 118, a snare 120 passed into the de-airing opening 130, down the cutting tool lumen 156 and out through the cutting blade 124, engages the guide suture, and is then pulled out through the de-airing opening 130 before the seating assembly 152 is joined to the blood vessel or other anatomical structure. Alternatively, if an endoscopic biopsy forceps is used, the snare 120 may, optionally, not be employed, as the jaws of the endoscopic biopsy forceps will engage with the anatomical tissue and the forceps will act as the guide. Guide member 118, therefore, serves two purposes; first, guide member 118 functions to position the graft housing 102, tubular graft 132 and seating assembly 152, and second, guide member functions to retain tissue cut by the cutting tool 122.

Once properly positioned, the staple ring 137, saddle flange 138, if present, and felt support ring 136 may be coupled by sutures, or preferably by a plurality of surgical staples 142. Where the staple ring 137 has a saddle flange 138 with a plurality of flange segments 140 and radial slots 144, each of the plurality of surgical staples 142 passes through pairs of radial slots 144 and bear against at least one of the plurality of saddle flange segments 140 when stapled. Where the staple ring 137 has either no saddle flange 138 or has a saddle flange 138 without flange segments 140 and radial slots 144, a plurality of staple apertures 141 is incorporated in the staple ring 137, as depicted in FIGS. 16A-17B. The plurality of surgical staples 142 pass into and through the plurality of staple apertures 141 and bear against the staple ring 137 when stapled. In this later embodiment, the surgical staples 142 are preferably pre-loaded into the staple apertures 141 of the staple ring 137.

Figure 18A:
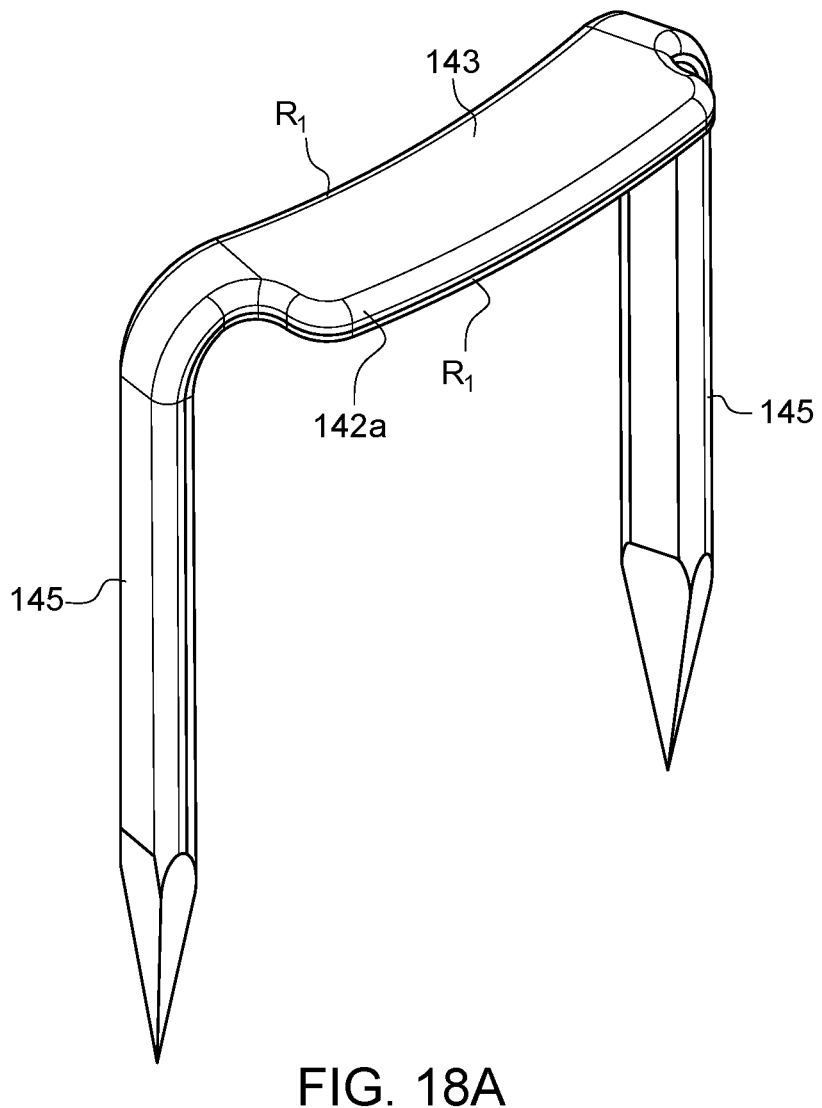
FIG. 18A is a perspective view of a first staple in accordance with the present disclosure.
Figure 18B:
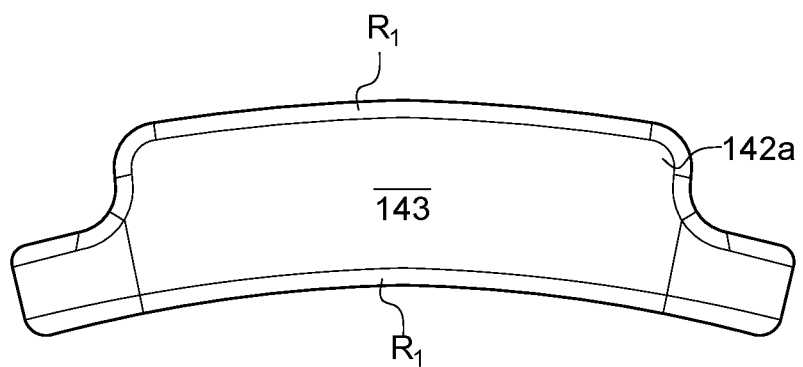
FIG. 18B is a top elevational view of the first staple in accordance with the present disclosure.
Figure 19A:
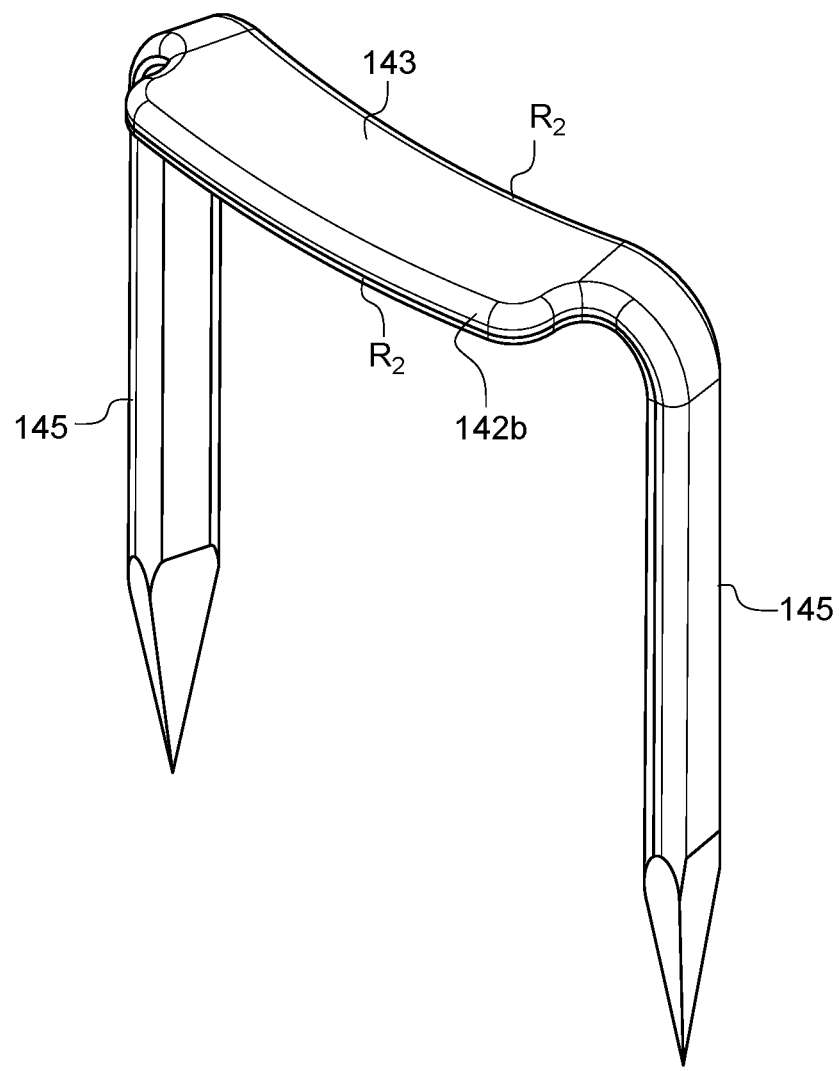
FIG. 19A is a perspective view of a second staple in accordance with the present disclosure.

Each of the plurality of surgical staples 142 passes through the staple ring 137, felt support ring 136, graft skirt 134, and into the tissue of the vessel or other anatomical structure to which the tubular graft 132 is being attached. The plurality of surgical staples 142 are preferably made of a shape memory material, such a Nitinol. As illustrated in FIGS. 18-19, each of the plurality of surgical staples 142 includes a staple head 143 and at least a pair of staple legs 145. When made of a shape memory material, each of the staple legs 145 has a pre-programed shape to extend outwardly along a longitudinal axis of the surgical staple 142 in an open configuration and curved along the radius curve of the staple ring 137 when fully deployed. By employing this pre-programmed open shape of the legs of surgical staples 142, the surgical staple 142 bites against a greater tissue surface area without having overlapping or interfering portions of the staple legs 145. Moreover, when the staple legs 145 are deployed, they exert a force vector toward the graft skirt 134, staple ring 137 and felt support ring 136 and through the tissue, thereby drawing the graft skirt 134, staple ring 137, felt support ring 136 and the aortic or anatomical tissue into closer approximation with one another.

Figure 19B:
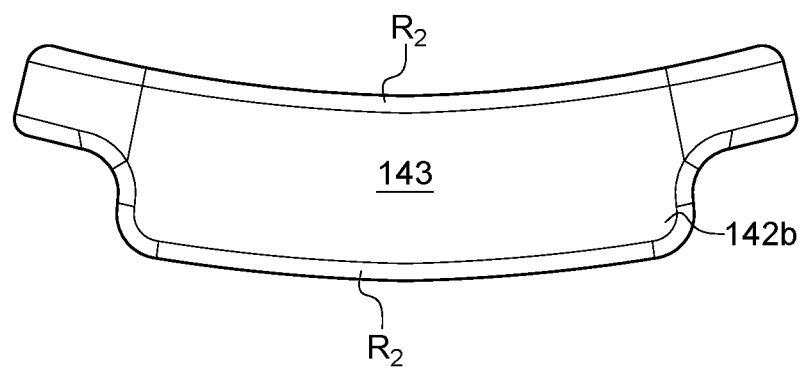
FIG. 19B is a top elevational view of the second staple in accordance with the present disclosure.

To further accommodate deployment of the plurality of surgical staples 142, and as illustrated in FIGS. 16A-19B, the staple apertures 141 include a first staple aperture 141A and a second staple aperture 141B. First staple aperture 141A has an opening profile matching profile of the staple head 143 for a corresponding first staple 142A. Second staple aperture 141B has an opening profile matching a profile of the staple head 143 for a corresponding second staple 142B. First staple 142A has a staple head profile that is generally quadrilateral with a first curvature $R_1$. Second staple 142B has a staple head profile that is generally quadrilateral with a second curvature $R_2$. $R_1$ and $R_2$ may be equal or different from each other. The generally quadrilateral profiles of each of first staple 142A and second staple 142B are contiguous with the staple legs 145 on each end of the staple head 143 along the longitudinal axis of each of the first staple 142A and second staple 142B. The first staple 142A has a staple head 143 that projects radially inward toward a center point of the staple ring 137. In contrast, second staple 142B has a staple head that projects radially outward away from the center point of staple ring 137. Similarly, first staple aperture 141A also has a generally quadrilateral opening profile with a first radius curvature $R_1$ that approximates the first radius curvature $R_1$ and staple head 143 orientation of the first staple 142A. Also similarly, second staple aperture 141B also has a generally quadrilateral opening profile with a second radius curvature $R_2$ that approximates the second radius curvature $R_2$ and staple head orientation of the second staple 142B. The staple legs 145 of each of the first staple 142A and second staple 142B are each offset to one side or the other side of the staple head 143, respectively, as shown in FIGS. 18 and 19. In this manner, the configurations of both the first staple aperture 141A and corresponding first staple 142A alternate positional orientation with an adjacent second staple aperture 141B and corresponding second staple 142B about the staple ring 137.

Once the staple ring 137, saddle flange 138, if present, felt support ring 136 and graft skirt 134 are secured to the vessel or other anatomical structure, if not already preloaded, the cutting tool 122 is introduced into the graft housing chamber 104. The cutting tool is engaged with the tissue to be cut and the cutting blade 124 is used to cut an opening or stoma in the vessel or anatomical structure. Once the opening or stoma is cut, the cut tissue tethered on the guide member 118 and the cutting blade 124 are withdrawn within the graft housing chamber 104 and the tubular graft 132 is clamped through the clamp opening 178 between the cutting blade 124 and the vessel or other anatomical structure to seal the tubular graft 132. Once the tubular graft 132 is clamped, the cutting tool 122, guide member 118, and the cut tissue may be removed from the tubular graft 132. Depending upon the configuration of the hemostatic coupling 108, the cutting tool 122 may be withdrawn through the hemostatic coupling 108, or the hemostatic coupling 108 may be removed to allow for withdrawal of the cutting tool 122 and replaced prior to stent delivery.

Next, the flanged stent 160 is delivered through the central lumen of tubular graft 132 and deployed within the opening formed in the blood vessel or anatomical structure and end-to-side anastomosis therewith. One or more delimiting stop collars 159 may also be provided either as an integral part of or removable from the pusher 148 and/or the inner delivery sheath 150. Stop collars 159 serve to demarcate a maximum position of the pusher 148 and/or the inner delivery sheath 150 during delivery of the tubular graft 132. These stop collars 159 serve to provide a guide to the physician of the relative positions of the pusher 148 and tubular graft 132 relative to the inner delivery sheath 150. Those skilled in the art will also understand that calendaring marks may be provided on the pusher 148 and/or inner delivery sheath 150 as indicia of the relative positioning instead of or in addition to the delimiting stop collars 159.

In operation, the proximal end 114 of graft housing 102 is joined to the hemostatic coupling 108, and the assembled stent delivery system 146 is introduced through the hemostatic coupling 108 and into central lumen of tubular graft 132 within the graft housing chamber 104. The centering balloon 156 is inflated against the inner walls of the tubular graft 132 to center the inner delivery sheath 150 carrying flanged stent 160 and outer delivery sheath 154 within the tubular graft 132, as shown in FIGS. 14A and 14B.

Figure 15A:
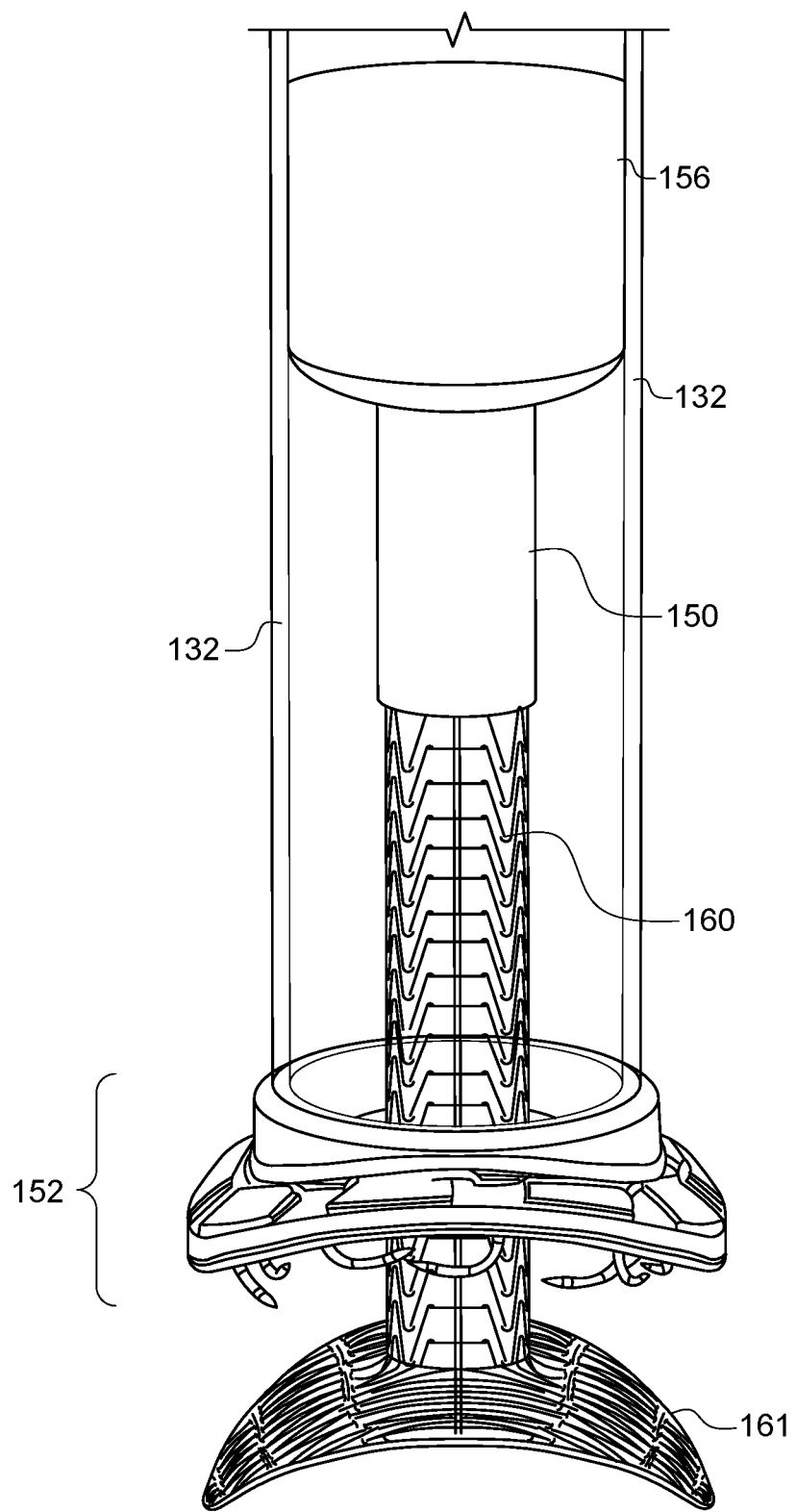
FIG. 15A is a perspective view illustrating expansion of the stent flange within the blood vessel or anatomical structure.
Figure 15B:
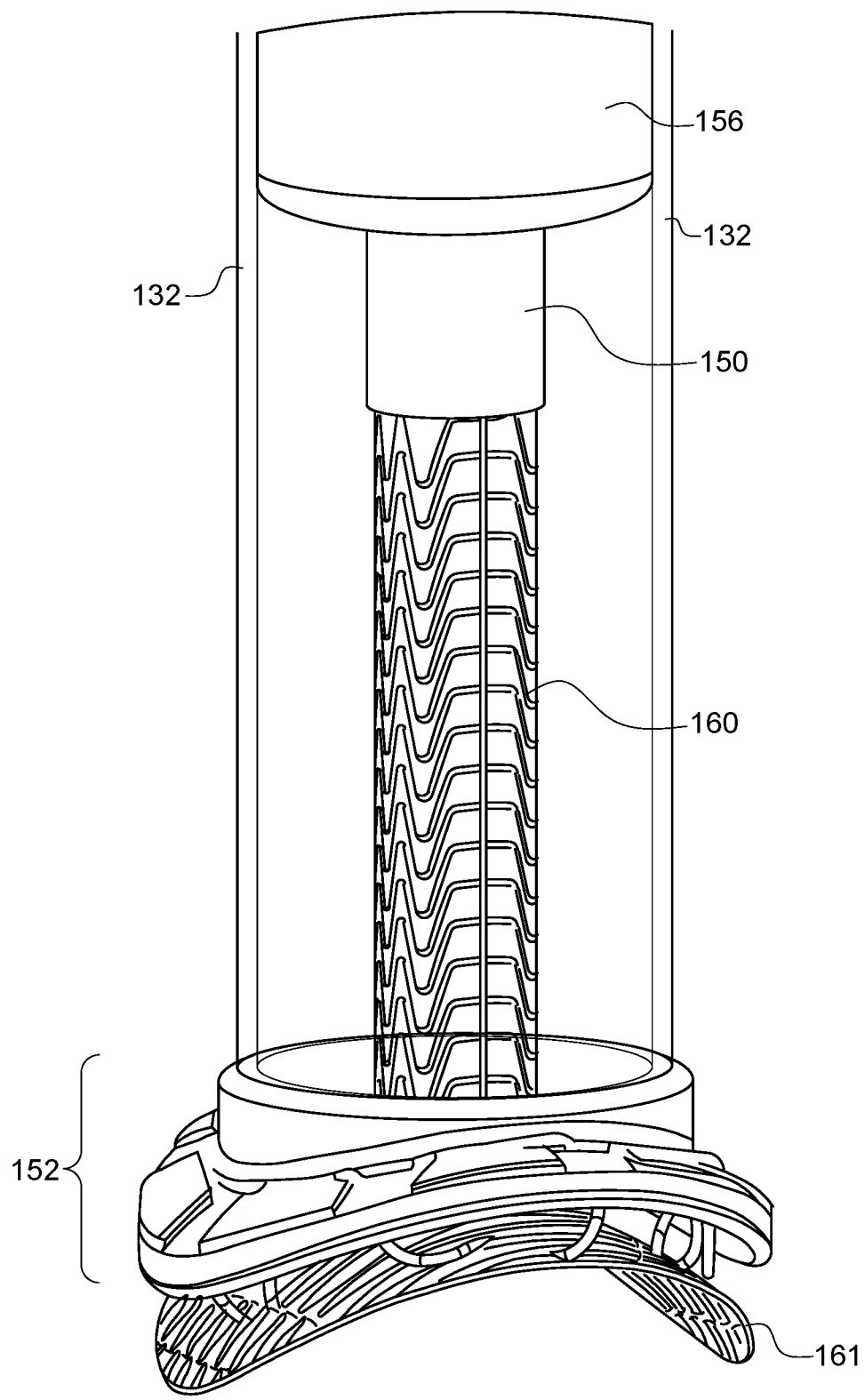
FIG. 15B is a perspective view illustrating apposition of the stent flange against a luminal wall of the blood vessel or anatomical structure.
Figure 16A:
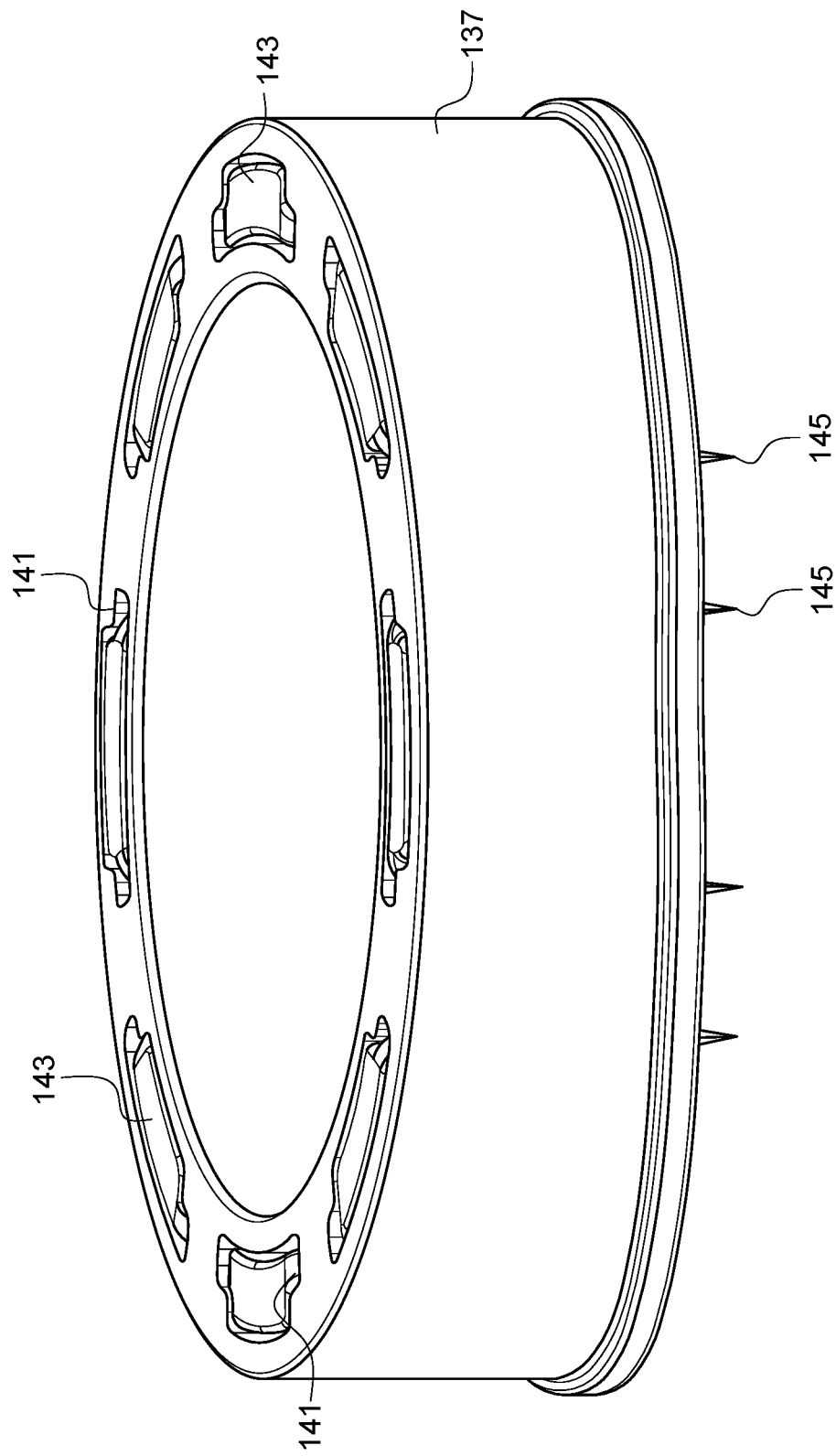
FIG. 16A is a perspective view of an embodiment of a staple ring in accordance with the present disclosure.
Figure 16B:
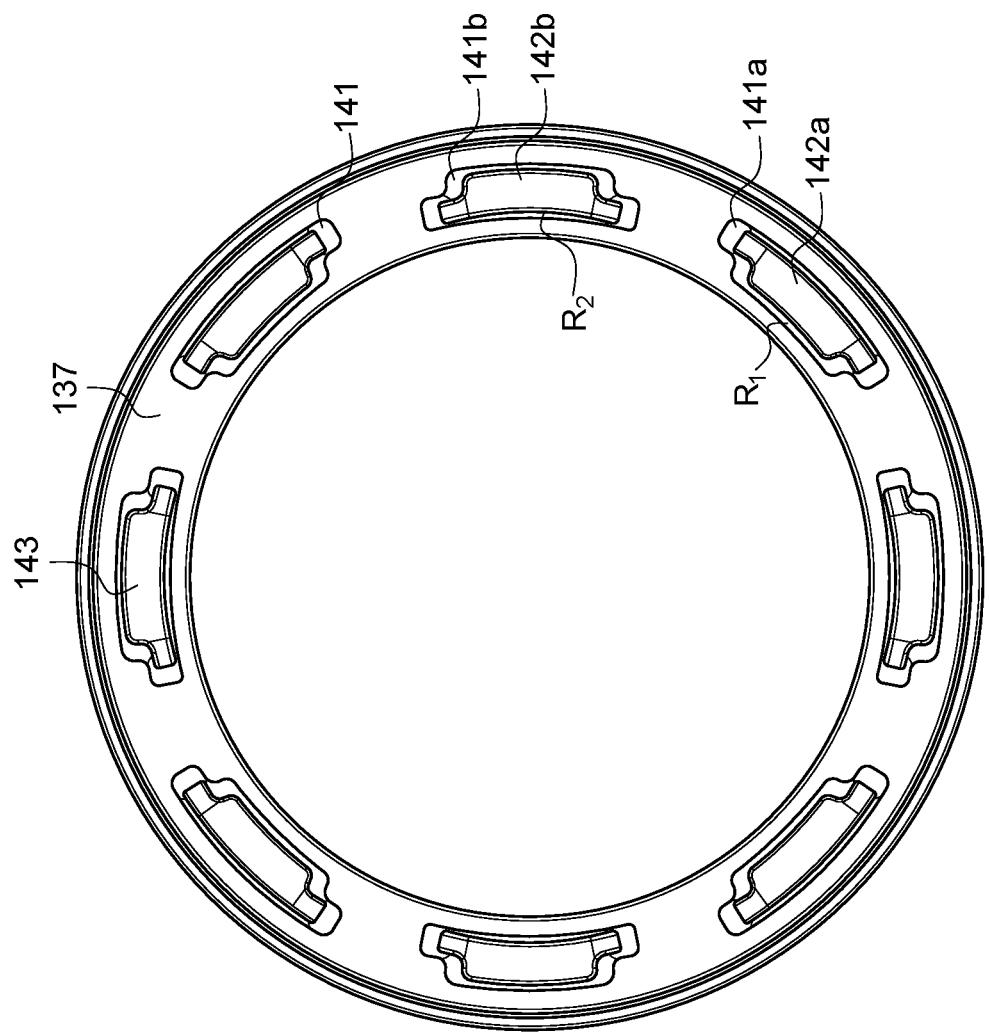
FIG. 16B is a top elevational view thereof.
Figure 17A:
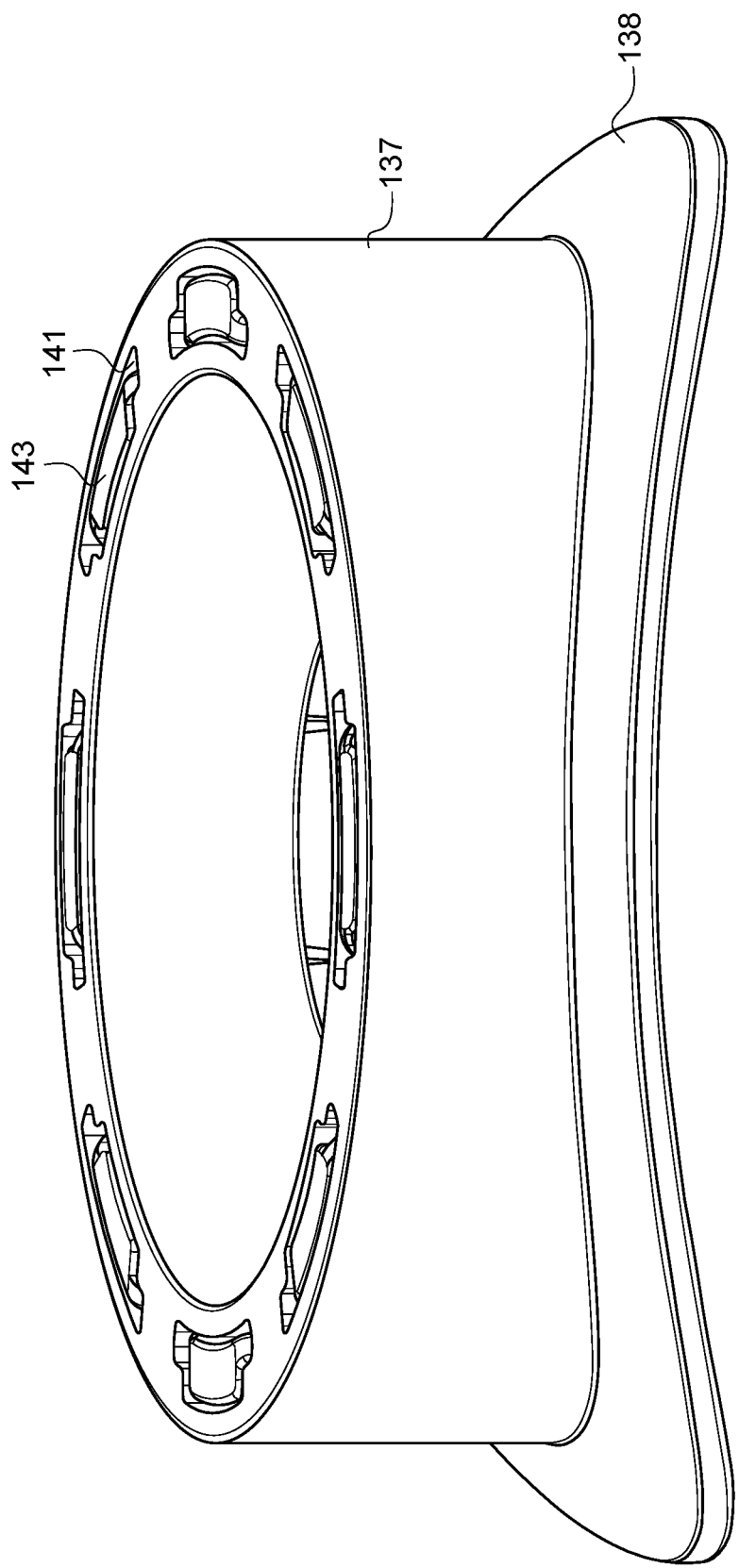
FIG. 17A is a perspective view of an alternative embodiment of a staple ring in accordance with the present invention.
Figure 17B:
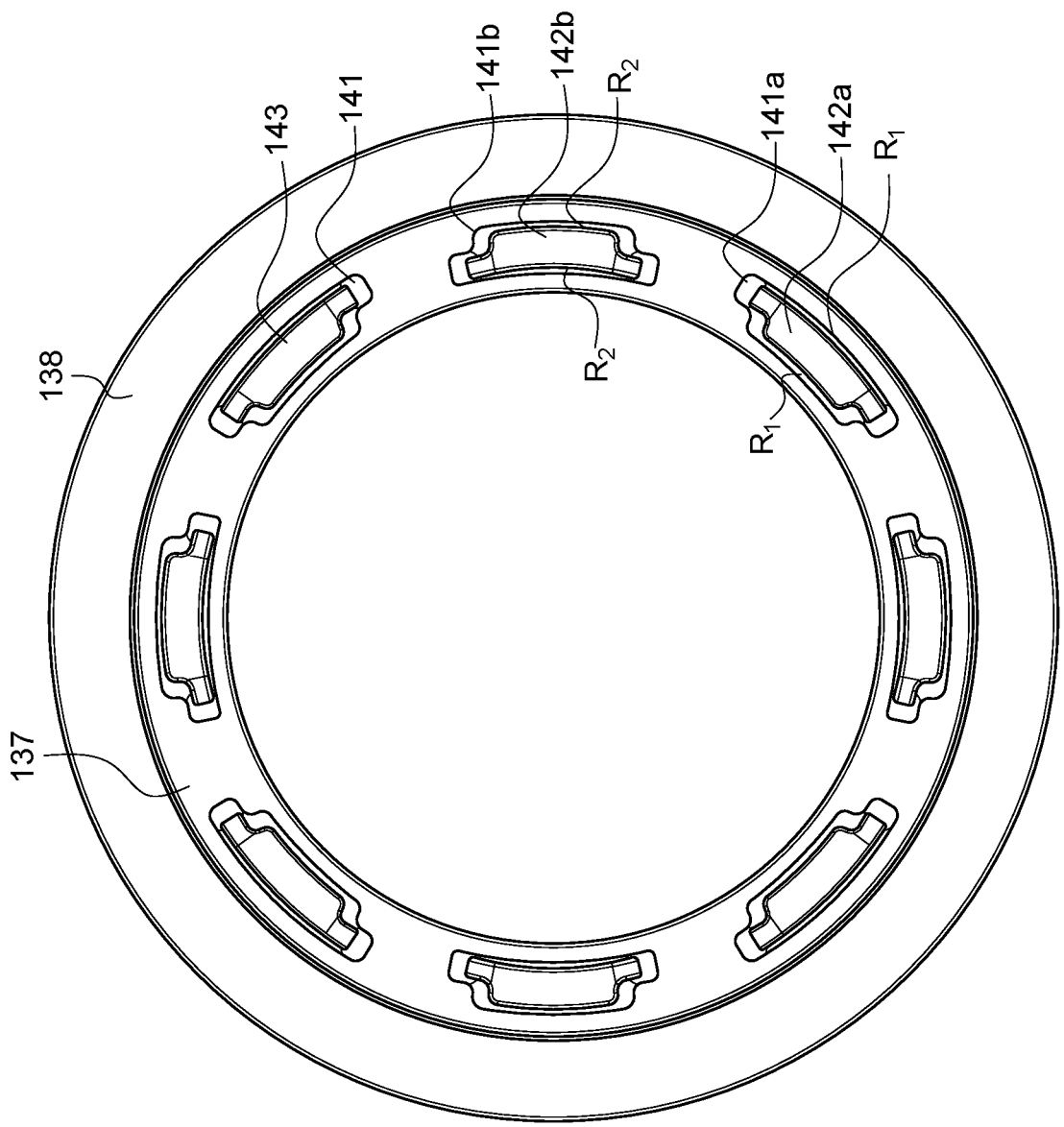
FIG. 17B is a top elevational view thereof.

As shown in FIGS. 15A and 15B, the pusher 148, inner delivery sheath 150, and flanged stent 160 are then pushed through the opening in the blood vessel or anatomical structure. Once properly positioned within the lumen of the blood vessel or anatomical structure, the inner delivery sheath 150 is partially withdrawn or the flanged stent 160 is pushed on pusher 148 a first distance to expose and release the stent flange 161 of flanged stent 160 allowing it to radially expand, as shown in FIG. 15A. The stent flange 161 may have a plurality of barbs 162 that project from a proximal surface of the stent flange 161.

As shown in FIG. 15B, once the stent flange 161 is radially expanded, the inner delivery sheath 150 and flanged stent 160 are then pulled back within the outer delivery sheath 154 thereby pulling the flanged stent 160 and stent flange 161 in a retrograde fashion a second distance until the stent flange 161 is in apposition with an inner wall or luminal surface of the blood vessel or anatomical structure. Where present, the optional plurality of barbs 162 on the stent will embed into the luminal surface of the blood vessel or anatomical structure and bear against the seating assembly 152 secured to the abluminal surface of the blood vessel or anatomical structure. Once the stent flange 161 is seated against the luminal surface of the blood vessel or anatomical structure, the inner delivery sheath 150 may be withdrawn to deploy the remainder of the flanged stent 160. The centering balloon 156 may deflated and the graft delivery system 146 withdrawn and removed from the tubular graft 132 and graft housing 102.

Once the graft delivery system 146 is withdrawn and the tubular graft 132 and flanged stent 160 are secured in an end-to-side anastomosis to the blood vessel or anatomical structure, the graft housing 102 may be removed and tubular graft 132 may be clamped proximal to the bypass connector 106 to seal the tubular graft 132, expose the tubular graft lumen 133 at its proximal end and, if desired, allow blood flow through the flanged stent 160 and distal end of tubular graft 132 and into the bypass connector 106 for cardiopulmonary bypass.

Figure 20:
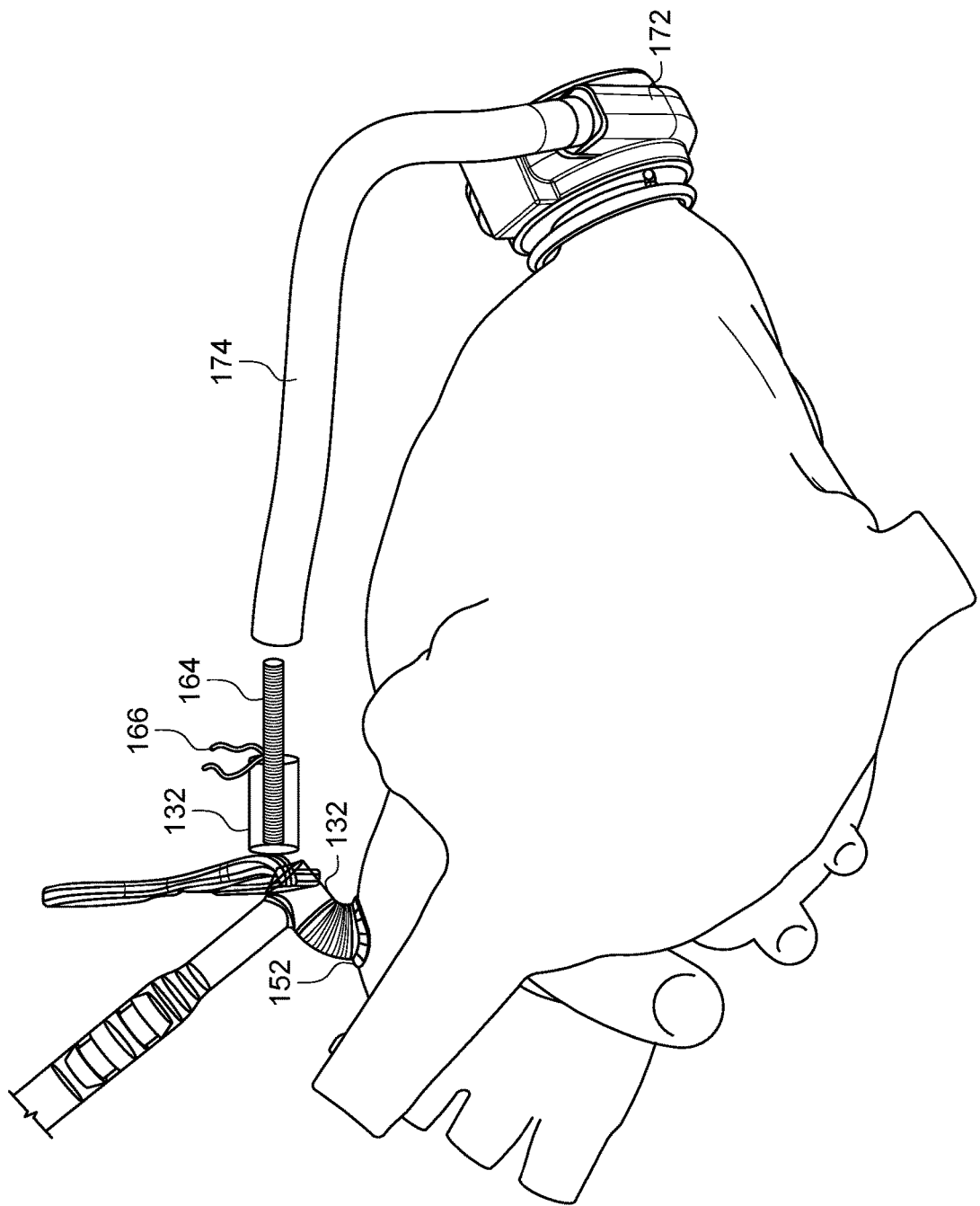
FIG. 20 is a perspective view of the end-to-end coupling positioned partially within a proximal end of the tubular graft in accordance with the present disclosure showing a VAD, a VAD conduit and a heart for illustrative purposes.
Figure 21:
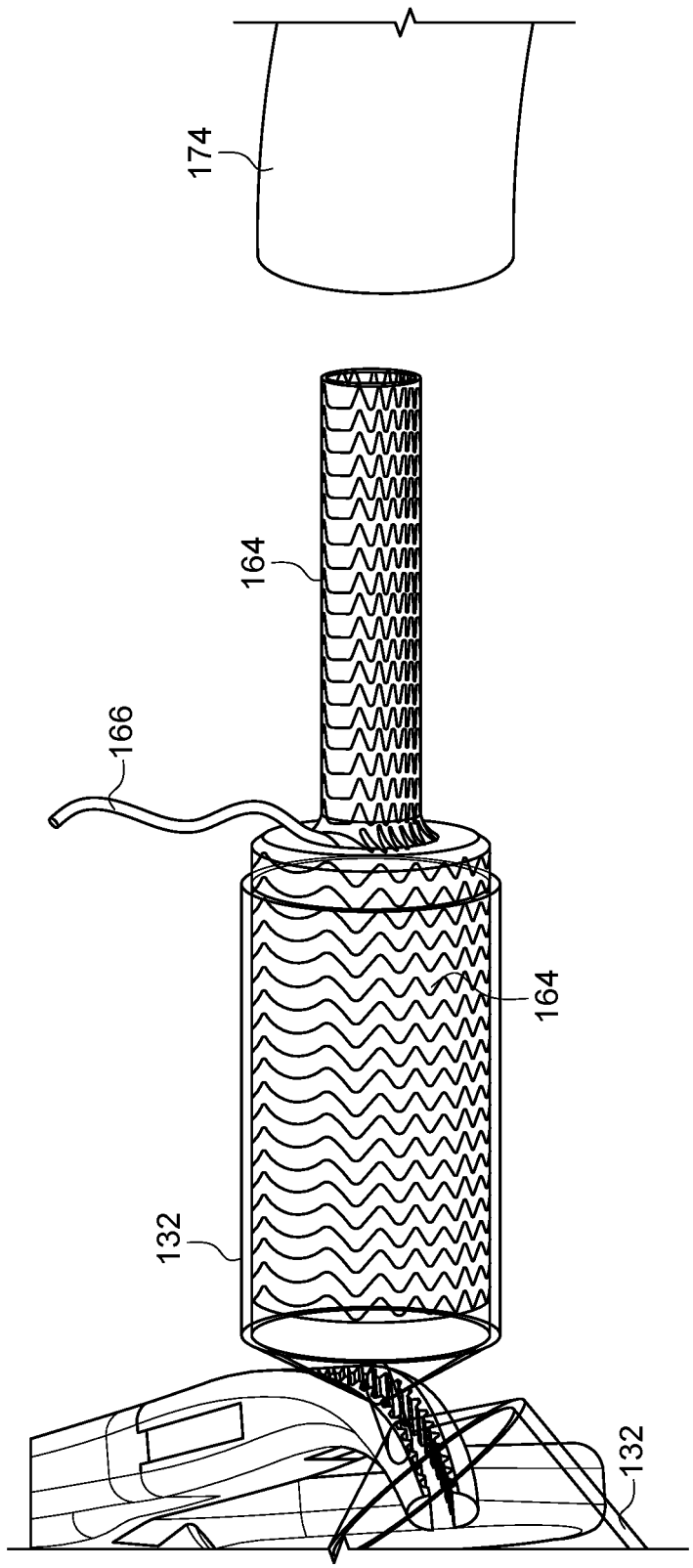
FIG. 21 is a perspective view of the end-to-end coupling diametrically expanded within the proximal end of the tubular graft and positioning of an LVAD conduit for coupling to the tubular graft in accordance with the present disclosure.

As shown in FIGS. 6A-6C and 20-22, an end-to-end coupling 164 is then coupled on one end to the proximal end of the tubular graft 132 and then coupled to a distal end of the LVAD conduit 174 placed in the proximal end of tubular graft lumen 133. The end-to-end coupling 164 may be a wide variety of connector devices that are capable of connecting the tubular graft 132 to the LVAD conduit 174 in an end-to-end manner. As an example of an end-to-end coupling 164, there is a diametrically expansive stent or stent-like member, such as a stent, stent-graft, or graft. The end-to-end coupling 164 may be: i) made of a shape memory material that is maintained below its transition temperature, such as in an ice bath, until employed and then exposed to a temperature above its transition temperature, such as by bathing in warm saline, to diametrically expand the end-to-end coupling 164, or ii) an elastic or shape memory device having an external constraint 166. In either instance, the end-to-end coupling 164 will bridge the interface between the tubular graft 132 and LVAD conduit 174. End-to end coupling 164 will be deployed in both the lumen of the proximal end of tubular graft 132 and the lumen of the distal end of the LVAD conduit 174. Deployment of end-to-end coupling 164 will allow it to diametrically expand from its diametrically compressed state, having a diameter $D_1$ to its diametrically expanded state, having a diameter $D_2$. End-to-end coupling 164 expandable member may be diametrically expanded from diameter $D_1$ to diameter $D_2$ along all or part of its length. It will be understood that both $D_1$ and $D_2$ are intended to be variables, are intended to be relative diametric values, that an expanded diameter $D_2$ may or may not be equal to another expanded diameter $D_2$, and that a diametrically compressed diameter $D_1$ may or may not be equal to another diametrically compressed diameter $D_1$. As shown in FIGS. 20-22, the end-to-end coupling 164 may be sequentially diametrically expanded where one portion is diametrically expanded within the tubular graft 132 and then and a second portion is diametrically expanded within the LVAD conduit 174 to complete the end-to end coupling.

External constraint 166 may be one or more removable tethers interlaced about the circumference of the end-to-end coupling, such as a bi-directional pull-chord or plural pull-cords, may be an external sheath having a frangible section to remove the sheath, or an external sheath that is removable through the lumen of the LVAD conduit 174. Once the proximal end of the tubular graft 132 and the distal end of the LVAD conduit 174 are brought into end-to-end apposition with each other, the expansion constraint 166 is either partially or fully released or the shape memory material is heated to allow for expansion so that the end-to-end connector bears against the inner wall surface of the respective lumens of the LVAD conduit 174 and tubular graft 132 thereby securing the same in end-to-end fluid communication with each other.

The end-to-end coupling 164 may be an encapsulated or covered stent such as that disclosed in U.S. Pat. No. 6,383,214 or 5,700,285, both of which are hereby incorporated by reference. Alternatively, the end-to-end coupling 164 may be a balloon expandable or shape memory stent with or without a covering. The covering, where employed, may cover only an intermediate longitudinal region of the stent where the tubular graft 132 and the LVAD conduit 174 join or abut, while proximal and distal end of the stent are uncovered and directly bear against the luminal wall surfaces of the tubular graft 132 and LVAD conduit 174.

Alternatively, the end-to-end coupling 164 may be made by a suture anastomosis or other mechanical connection.

Finally, the end-to-end coupling 164 may be eliminated entirely, by simply extending the proximal end of the tubular graft 132 to span a length from the graft skirt 134 to the LVAD pump 172. In this variant, the tubular graft 132 effectively replaces the LVAD conduit 174 while also eliminating the need for the end-to-end coupling 164. According to this variant of tubular graft 132, the graft delivery system 146 would need to be modified to accommodate for the longer length of the proximal end of tubular graft 132 and any features as may be required for connection to a particular VAD.

Once the end-to-end coupling 164 is fully deployed and the LVAD conduit 174 and tubular graft 132 are coupled in fluid flow communication, the connection to the aorta or other anatomic structure is completed as shown in FIG. 22. Of course, if the end-to-end coupling 164 is eliminated, along with the LVAD conduit 174, and the tubular graft 132 is extended in length, simply coupling the proximal end of the tubular graft 132 to the LVAD pump 172 will complete the fluid pathway.

Turning now to the method 200 of the present disclosure, which is diagrammatically illustrated in FIG. 23. For purposes of clarity, each method step will be referred to as "Step 1, Step 2, Step 3, etc."

Step 1. 202 A guide member 118 is fixed at the center of the intended implant site on the target vessel, according to various embodiments described herein.

Step 2. 204 The suture snare 120 is then used to pull the guide member 118 into and through the cutting tool lumen 126, cutting tool handle 128 and exposing the guide member through the de-airing opening 130. As noted above, the use of suture snare 120 in this step 2 204 may be eliminated where the guide member 118 is not a suture and another type of guide member 118, such as an endoscopic biopsy forceps, is employed.

Step 3. 206 The graft housing 102, tubular graft 132, seating assembly 152, and cutting tool 122 are then placed over the intended implant site. The seating assembly 152 at the distal end of the tubular graft 132 and graft housing 102 is placed in abutting relationship with the intended implant site on the blood vessel or anatomic structure, with either the felt support ring 136 or the graft skirt 134 abutting the implant site and staple ring 137 bearing against the graft skirt 134 and felt support ring 136. Steps 2 and 3 may be performed in the order recited or may be performed in reverse order.

Step 4. 208 The seating assembly 152, including the staple ring 137, graft skirt 134, and felt support ring 136, are then affixed to the target vessel or anatomic structure. As discussed above, affixation may be made by employing surgical staples 142 that pass through the staple ring 137, either through staple apertures 141 or through the radial slots 144 between the saddle flange segments 140. Staple legs 145 pass through the staple ring 137, the felt support ring 136 and the graft skirt 134 and into the target vessel or anatomic structure. As also discussed above, the staple legs 145 preferably, but not necessarily deform outwardly away from the staple head 143 of the each surgical staple 142 to increase the biting surface area within the blood vessel or other anatomical structure, not interfere with adjacent staples 142 and exert a compressive force against the staple ring 137, graft skirt 134, felt support ring 136 and aortic or anatomical tissue. This outward deformation may occur by shape memory properties of the material of the surgical staples 142 or by a stapler having an appropriate anvil that the legs bear against during stapling. Plural surgical staples 142 are used to staple each of the saddle flange segments 140 about the entire circumference of the saddle flange 138, or around the circumference of the saddle flange 138 when the saddle flange segments 140 are not present, or around the circumference of the staple ring 137 where the saddle flange 138 is not present or not employed for fixation to the target vessel or anatomic structure.

In other embodiments a single continuous shape memory staple with multiple penetrating arms may be deployed in a single actuation to be deployed around the circumference of the rigid or semi-rigid support flange. Other embodiments may employ 2, 4, or more surgical staples 142 with multiple arms deployed simultaneously or sequentially. In other embodiments, a plurality of single staples may be deployed simultaneously or sequentially around the circumference of the conduit connection using a single actuating mechanism or a separate stapling tool.

Step 5. 210 The target blood vessel or anatomic structure is then cored to create the opening for the end-to-side anastomosis. The target tissue is resected using the cutting blade 124 and controlling the resected tissue using the guide member 118. De-airing may occur spontaneously through the cutting tool lumen 126 and de-airing opening 130. Once the target tissue is cut, the tissue segment is retained on the guide member 118 within the cutting blade 124, and the cutting tool 122 is withdrawn into an upper section of the graft housing chamber 104 and below the hemostatic coupling 108.

Step 6. 212 The cutting tool 122, guide member 118 and cut tissue is then removed under hemostasis by clamping the tubular graft 132 below the cutting blade 124. The access openings 178 in the graft housing 102 may be used for clamp access to the tubular graft 132. After the tubular graft 132 is clamped, the cutting tool 122, guide member 118 and cut tissue may be removed from the tubular graft 132 and graft housing 102.

Step 7. 214 If removed, the hemostatic coupling 108 may then be replaced at the proximal end of the tubular graft 132 and graft housing 102, the clamp removed from Step 6 212, and the stent delivery system 146 is introduced into the central lumen of tubular graft 132 through the hemostatic coupling 108. As discussed above, the stent delivery system 146 includes the flanged stent 160 for delivery to and deployment at the implant site at the distal end of the graft housing chamber 104.

Step 8. 216 Once positioned within the central lumen of tubular graft 132, the centering balloon 156 may be inflated against the walls of the tubular graft 132 to center the outer delivery sheath 154, inner delivery sheath 150, pusher 148, and flanged stent 160 in axial alignment with the opening in the blood vessel or anatomical structure.

Step 9. 218 The distal end of the flanged stent 160 having the stent flange 161 is then placed into and through the opening in the blood vessel or anatomical structure using the pusher 148 and inner delivery sheath 150. Once the distal end of the tubular graft 132 is in a desired position, the inner delivery sheath 150 is either withdrawn or the pusher 148 extended to expose the stent flange 161 thereby allowing it to radially expand to its saddle-like deployed shape while the remainder of the flanged stent 160 remains constrained on the pusher 148 by the inner delivery sheath 150.

Step 10. 220 When the flanged stent 160 and stent flange 161 are positioned in a desired position within the opening of the blood vessel or anatomical structure, the pusher 148 and inner delivery sheath 150 are axially withdrawn through the outer delivery sheath 154 to position the stent flange 161 in abutting relationship with the luminal surface of the blood vessel or anatomical structure.

Step 11. 222 The expanded stent flange 161 is then affixed to the luminal surface of the blood vessel or anatomical structure embedding in the luminal surface of the blood vessel or anatomical structure. Seating the expanded stent flange 161 against the luminal wall surface of the blood vessel or other anatomical structure may be sufficient to anchor the stent 160 and the tubular graft 132. The plurality of barbs 162 on the stent flange 161 may optionally be employed to further anchor the stent 160 and the tubular graft 132.

Step 12. 224 Once the stent flange 161 is secured against the luminal surface of the blood vessel or anatomical structure, the inner delivery sheath 150 is withdrawn to expose the remainder of the flanged stent 160 allowing it to diametrically expand and release from the pusher 148 within the central lumen of tubular graft 132 within the graft housing chamber 104. Thereafter, the centering balloon 156 is deflated and the stent delivery system 146 is removed.

Step 13. 226 Optionally, in circumstances in which cardiopulmonary bypass is required, the bypass connector 106 is coupled to an arterial tubing line of a heart-lung machine.

Step 14. 228 The graft housing 102 may then be removed from the tubular graft 132. After clamping the tubular graft 132 proximal to the bypass connector 106, if provided, a valve or clamp on the bypass connector 106 is opened to initiate arterial blood flow from the heart-lung machine. Step 13, 226, and step 14, 228, may, optionally be performed in reverse order.

Step 15. 229 Tubular graft 132 may then be cut to remove the hemostatic coupling 108 and trimmed to a desired length.

Step 16. 230 An end-to-end coupling is then made between the proximal end of the tubular graft 132 and the LVAD conduit 174 to complete the fluid pathway. Alternatively, where the tubular graft 132 is of the elongated variant, Step 16 230 may be replaced by simply joining the proximal end of the tubular graft 132 to the LVAD pump 172. Once the end-to-end coupling is completed and cardiopulmonary bypass discontinued, the bypass connector 106 may be removed, such as by cutting and stapling, or other means of forming a closure of the bypass connector opening adjacent to the wall of the tubular graft 132.

In some embodiments (not shown), further external support of the end-to-end coupling connection may be desired. In this circumstance, an externally placed shape memory or superelastic diametrically contracting stent, which may be covered or uncovered, may be placed on the abluminal or outer walls and over the proximal end of the tubular graft 132 or the distal end of the LVAD conduit 174 prior to deployment of the end-to-end coupling 164. Following deployment of the end-to-end coupling 164, the external diametrically contracting stent may positioned on the abluminal or outer wall surfaces and bridge the interface between the proximal end of tubular graft 132 and the distal end of the LVAD conduit 174 and then deployed to contract over the end-to-end coupling and bridge the interface. The external stent may be deployed by several mechanisms including: removal of an internal constraining sheath, removal of a peel-away external coating, removal of another form of external constraint, or temperature change to effectuate the transformation temperature of a shape memory material for the external stent. This list is not intended to exclude any other potential means of deploying an external diametrically contracting stent.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented or claimed, unless expressly specified otherwise. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

The invention claimed is:

1. A tubular graft assembly configured to be attached to a side of a tubular anatomical structure, comprising:
   a primary graft conduit having a circumferential distal end skirt, a proximal end, wherein the stent is a first stent, and the tubular graft assembly further comprises a second stent, wherein the second stent is covered and is configured to facilitate coupling the proximal end of the primary graft conduit with a separate graft conduit;
   a stent having a tubular portion and a circumferential flange portion;
   an external annular support having a plurality of tissue anchor openings passing axially there through, wherein the external annular support further comprises an annular ring having a plurality of staple openings passing longitudinally through the annular ring, each of the plurality of staple openings having a generally quadrilateral shaped profile, and a substantially saddle shaped flange extending radially from the annular ring;
   a plurality of tissue anchors configured to pass axially into and through the tissue anchor openings of the external annular support, the plurality of tissue anchors further comprising a plurality of staples, each of the plurality of staples having a generally quadrilateral shaped planar head that matches the generally quadrilateral profile of the plurality of staple openings;
   wherein in an installed state the tubular portion of the stent is disposed within the primary graft conduit, the distal end skirt is engaged against an outer wall surface of the tubular anatomical structure, the circumferential flange portion of the stent is extended distally beyond the distal end skirt and into the tubular anatomical structure, and the circumferential flange portion of the stent engages against the inner wall surface of the tubular anatomical structure and the external annular support is concentrically engaged about the primary graft conduit and against the circumferential distal end skirt; and
   wherein in the installed state at least a portion of the tubular anatomical structure is compressed between the distal end skirt and the flange portion of the stent.

2. The tubular graft assembly of claim 1, wherein the plurality of staples further comprises a first staple having a first generally quadrilateral profile and a second staple having a second generally quadrilateral profile.

3. The tubular graft assembly of claim 2, wherein the first generally quadrilateral profile and the second generally quadrilateral profile are mirror images of each other.

4. The tubular graft assembly of claim 3, wherein adjacent pairs of the plurality of staple openings are radially offset from each other about the annular ring.

5. The tubular graft assembly of claim 4, wherein the plurality of staple openings have an opening profile that matches the shape of the first generally quadrilateral profile and the second generally quadrilateral profile of the first staple and second staple, respectively.

6. The tubular graft assembly of claim 3, wherein each of the plurality of staples are made of a shape-memory material and further has a least two legs, the at least two legs having a pre-programmed shape that projects the at least two legs away from the staple head along a longitudinal axis of the staple when deployed in the anatomical structure.

7. A tubular graft assembly configured to be attached to a side of a tubular anatomical structure, comprising:
   a primary graft conduit having a distal end skirt;
   a stent having a tubular portion and a flange portion;
   an annular ring having a plurality of staple openings having a generally quadrilateral profile and passing longitudinally through the annular ring and having a substantially saddle-shaped flange extending radially from the annular ring, wherein adjacent pairs of the plurality of staple openings are radially offset from each other about the annular ring;
   a plurality of staples, each of the plurality of staples having a generally quadrilateral shaped planar head that matches the generally quadrilateral profile of the plurality of staple openings;
   wherein in an installed state the tubular portion of the stent is disposed within the primary graft conduit, the distal end skirt is engaged against an outer wall surface of the tubular anatomical structure, the flange portion of the stent is extended distally beyond the distal end skirt, and the flange portion of the stent engages against the inner wall surface of the tubular anatomical structure; and
   wherein in the installed state at least a portion of the tubular anatomical structure is compressed between the distal end skirt and the flange portion of the stent.

8. The tubular graft assembly of claim 7, wherein the generally quadrilateral profile of the plurality of staple openings further comprises a first generally quadrilateral profile and a second generally quadrilateral profile that are mirror images of each other.

9. The tubular graft assembly of claim 7, wherein adjacent pairs of the plurality of staple openings are radially offset from each other about the annular ring.

10. The tubular graft assembly of claim 7, wherein each of the plurality of staples are made of a shape memory material and further has a least two legs, the at least two legs having a pre-programed shape memory shape that projects the at least two legs away from the staple head along a longitudinal axis of the staple when deployed in the anatomical structure.

\* \* \* \* \*